(12) United States Patent
Wilson et al.

(10) Patent No.: US 10,966,800 B2
(45) Date of Patent: *Apr. 6, 2021

(54) TWO-PIECE BILATERAL ILLUMINATION ATTACHMENT FOR DENTAL CAMERA

(71) Applicant: Digital Doc LLC, El Dorado Hills, CA (US)

(72) Inventors: David D. Wilson, El Dorado Hills, CA (US); John W. Sellers, El Dorado Hills, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/034,270

(22) Filed: Jul. 12, 2018

(65) Prior Publication Data

US 2019/0110863 A1 Apr. 18, 2019

Related U.S. Application Data

(63) Continuation-in-part of application No. 15/786,905, filed on Oct. 18, 2017, now Pat. No. 10,258,227.

(51) Int. Cl.
*A61C 1/08* (2006.01)
*A61B 5/00* (2006.01)

(52) U.S. Cl.
CPC ............ *A61C 1/088* (2013.01); *A61B 5/0088* (2013.01); *A61B 2562/227* (2013.01); *A61B 2562/228* (2013.01); *A61C 2204/002* (2013.01)

(58) Field of Classification Search
CPC ......... A61B 1/06; A61B 1/24; A61B 1/00096; G03B 15/14; A61C 1/088
USPC .......................................................... 433/29
See application file for complete search history.

(56) References Cited

U.S. PATENT DOCUMENTS

| 5,115,307 | A  | * | 5/1992 | Cooper | A61B 1/00091 348/66 |
| 7,717,709 | B2 | * | 5/2010 | Kobayashi | A61B 1/0008 433/29 |
| 2005/0200707 | A1 | * | 9/2005 | Yogesan | A61B 1/24 348/207.99 |
| 2012/0122051 | A1 | * | 5/2012 | Hackel | A61B 1/0684 433/29 |
| 2012/0122053 | A1 | * | 5/2012 | Hackel | A61B 1/00186 433/29 |
| 2013/0034826 | A1 | * | 2/2013 | Walsh | A61B 5/4547 433/29 |
| 2013/0158350 | A1 | * | 6/2013 | Juergens | A61B 1/00114 600/109 |

(Continued)

*Primary Examiner* — Matthew M Nelson
(74) *Attorney, Agent, or Firm* — Craig A. Simmermon

(57) ABSTRACT

Two-piece bilateral illumination attachment for dental camera is a light source that is reversibly attachable to any dental camera. Two-piece bilateral illumination attachment for dental camera has two light sources that directly face each other. When properly attached to a dental camera, two-piece bilateral illumination attachment for dental camera effectuates sub-enamel illumination or bilateral illumination of a tooth, so that the dental camera may capture a photo or image of the illuminated tooth. Two-piece bilateral illumination attachment for dental camera has a specially shaped body that makes a slip-fit, press-fit, or snap-fit onto the exterior surface of any dental camera. Two-piece bilateral illumination attachment for dental camera has a distal section and a proximal section. The distal section is reversibly attachable to the proximal section. The distal section is sterilizeable.

4 Claims, 16 Drawing Sheets

(56) References Cited

U.S. PATENT DOCUMENTS

2014/0377716 A1\* 12/2014 Rauscher ............. A61C 19/004
              433/29
2015/0079535 A1\* 3/2015 Hollenbeck ............ A61B 1/253
              433/29
2017/0215997 A1\* 8/2017 Martin .................... A61C 9/008

\* cited by examiner

001 # TWO-PIECE BILATERAL ILLUMINATION ATTACHMENT FOR DENTAL CAMERA

CROSS-REFERENCE TO RELATED APPLICATIONS

The instant application is a continuation-in-part of U.S. application Ser. No. 15/786,905 entitled "BILATERAL ILLUMINATION ATTACHMENT FOR DENTAL CAMERA" filed on Oct. 18, 2017, which is hereby incorporated by reference herein.

BACKGROUND OF THE INVENTION

1. Field of the Invention

This invention relates to sub-enamel illumination or bilateral illumination of a tooth. Sub-enamel illumination or bilateral illumination is the process of projecting light into the interior of the tooth from both the buccal side of the tooth and the lingual side of the tooth where this light is scattered in the interior of the tooth to exit the tooth from the coronal surface. An image is then taken or recorded from the scattered light emerging from the coronal surface of the tooth where this image is used to help determine and categorize any impurities that might be present in the tooth such as fractures, leaking amalgam, decay, and the like. Specifically, this invention is an illumination attachment that is reversibly attachable to any dental camera. The illumination attachment functions to project light into the buccal side of the tooth and the lingual side of the tooth. The dental camera functions to capture the image of the scattered light emerging from the coronal surface of the tooth. The dental camera is not a portion of this invention.

2. Description of Related Art

There are stand-alone devices in the prior art that effectuate sub-enamel illumination or bilateral illumination of a tooth and record an image of sub-enamel illumination or bilateral illumination of the tooth. However, there are no lighting devices in the prior art other than this one that are reversibly attachable to an existing dental camera in order to effectuate sub-enamel illumination or bilateral illumination of a tooth so that the existing dental camera may capture an image of sub-enamel illumination or bilateral illumination of the tooth.

BRIEF SUMMARY OF THE INVENTION

It is an aspect of two-piece bilateral illumination attachment for dental camera to be reversibly attachable to any dental camera.

It is an aspect of two-piece bilateral illumination attachment for dental camera to effectuate sub-enamel illumination or bilateral illumination of a tooth.

It is an aspect of two-piece bilateral illumination attachment for dental camera to have a distal section and a proximal section that are reversibly attachable to each other.

It is an aspect of the distal section of two-piece bilateral illumination attachment for dental camera to be sterilizeable.

It is an aspect of the distal section of two-piece bilateral illumination attachment for dental camera to include a dual light tooth cup.

It is an aspect of dual light tooth cup to have a left arm with a first light source and a right arm with a second light source.

It is an aspect of dual light tooth cup to be sterilizeable.

It is an aspect of the proximal section of two-piece bilateral illumination attachment for dental camera to include a circuit board and a battery.

It is an aspect of two-piece bilateral illumination attachment for dental camera to include a means to reversible detach the distal section from the proximal section so that the distal section may be separated from proximal section and sterilized without damaging the circuit board or battery in the proximal section.

It is an aspect of two-piece bilateral illumination attachment for dental camera to include a means to reversible attach the distal section to the proximal section wherein electrical continuity is created between the battery and the first and second light source when attached.

DEFINITION LIST

Figure 1:
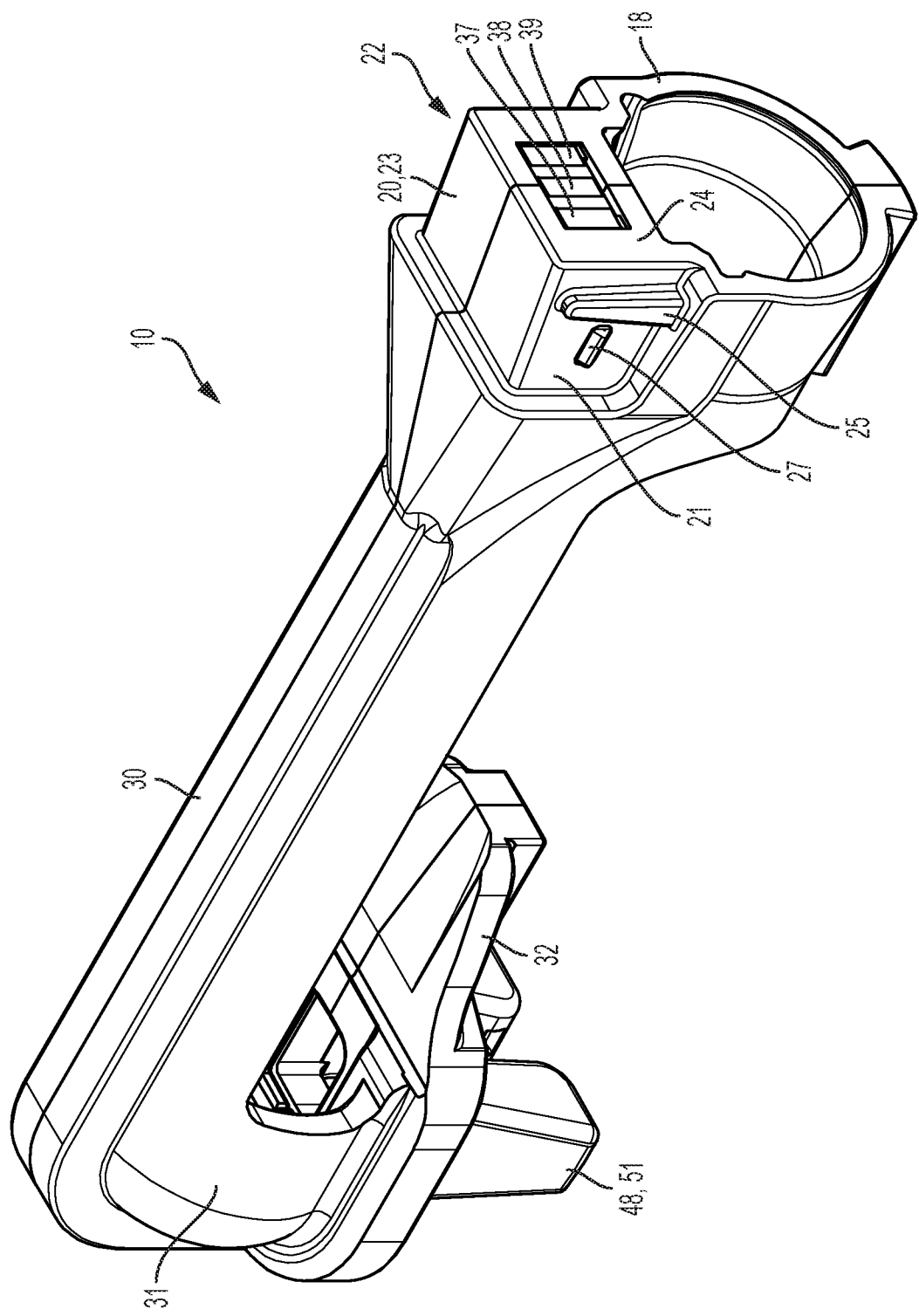
FIG. 1 is a perspective view of the distal section of two-piece bilateral illumination attachment for dental camera.
Figure 2:
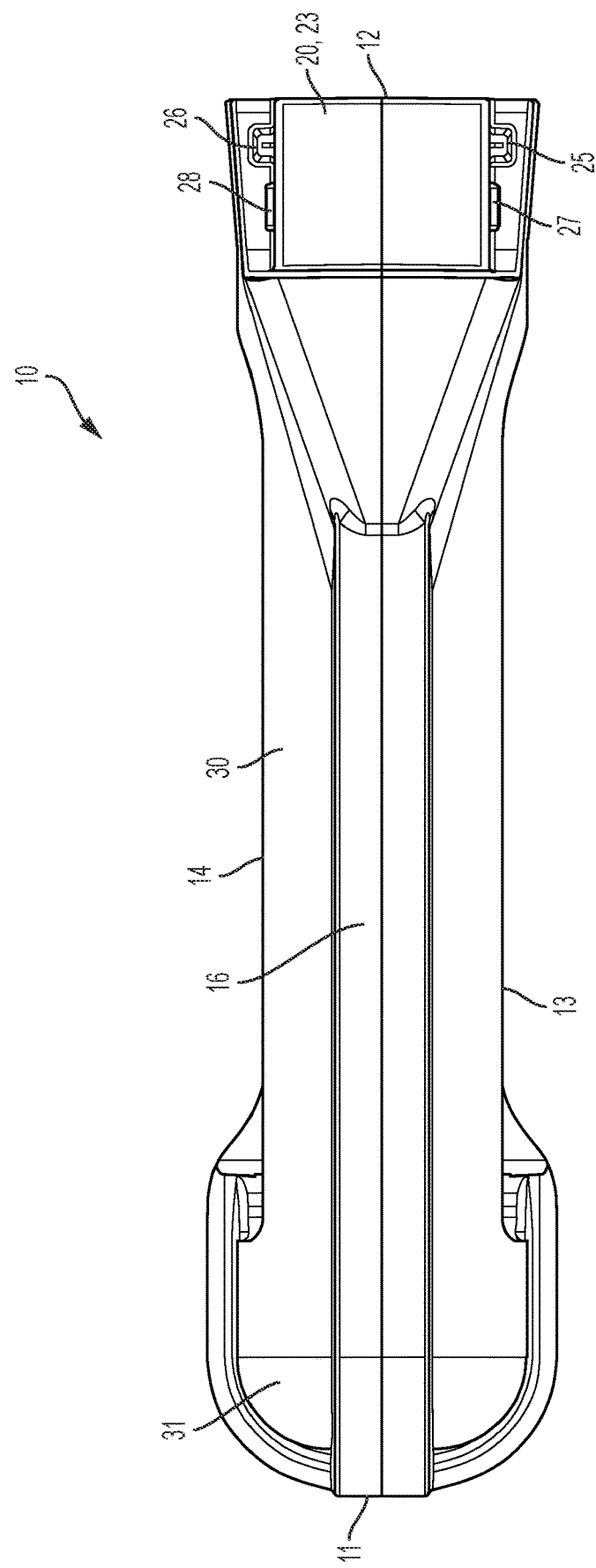
FIG. 2 is a top plan view of the distal section of two-piece bilateral illumination attachment for dental camera.
Figure 3:
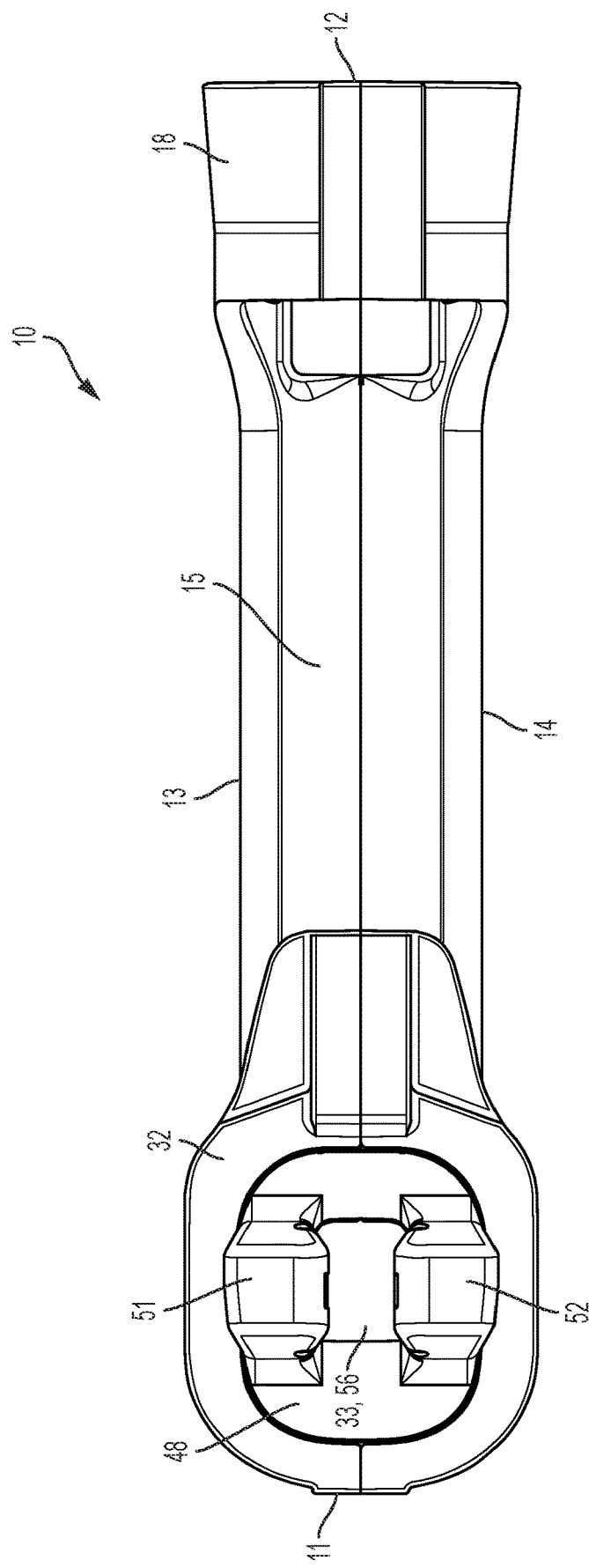
FIG. 3 is a bottom plan view of the distal section of two-piece bilateral illumination attachment for dental camera.
Figure 4:
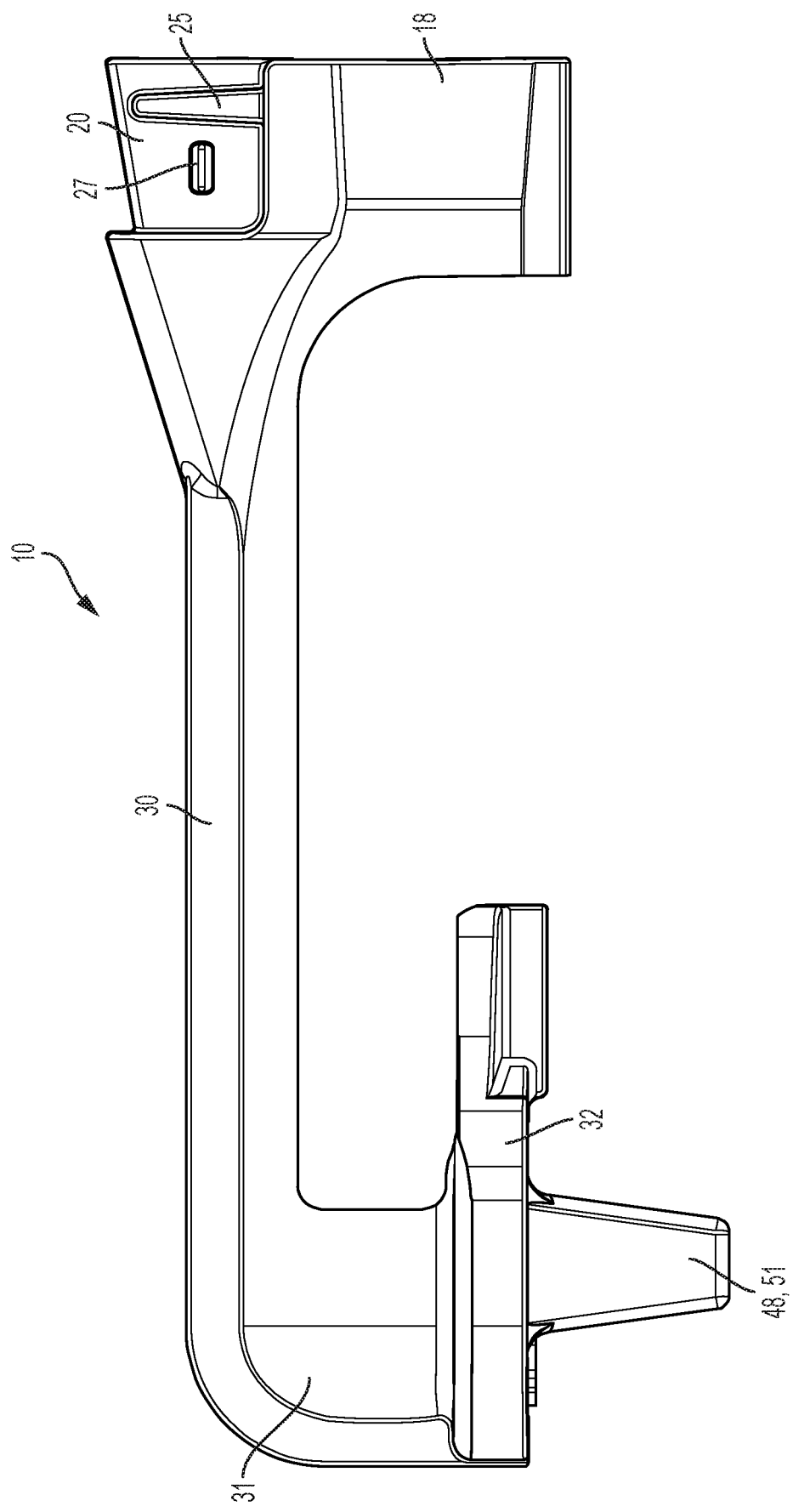
FIG. 4 is a left side elevation view of the distal section of the distal section of two-piece bilateral illumination attachment for dental camera.
Figure 5:
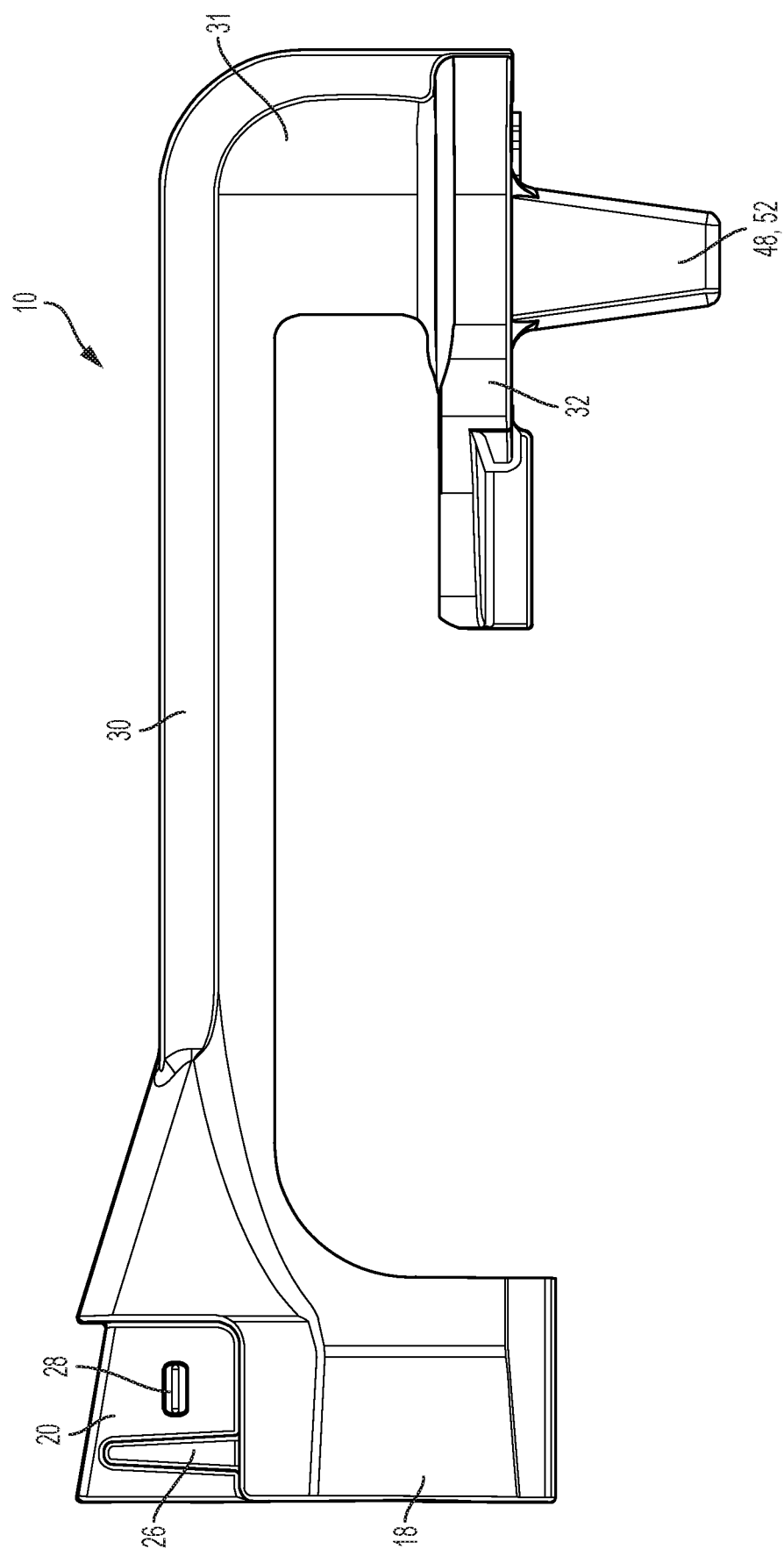
FIG. 5 is a right side elevation view of the distal section of two-piece bilateral illumination attachment for dental camera.
Figure 6:
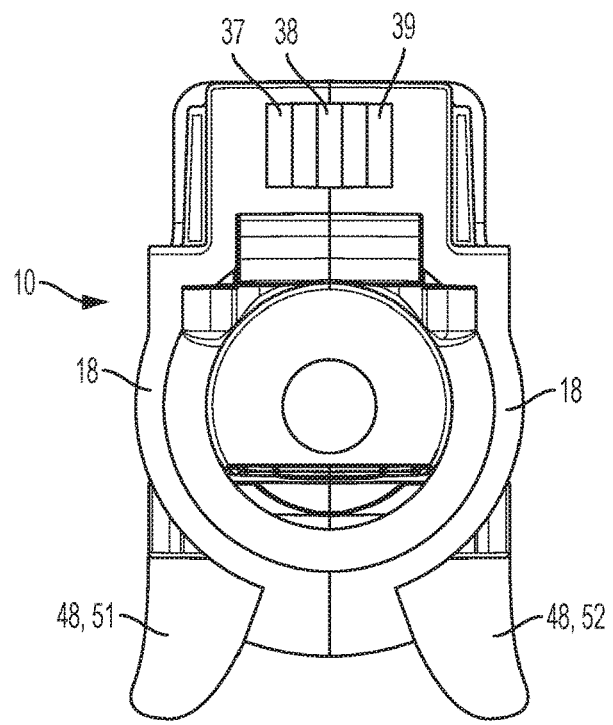
FIG. 6 is a rear elevation view of the distal section of two-piece bilateral illumination attachment for dental camera.
Figure 7:
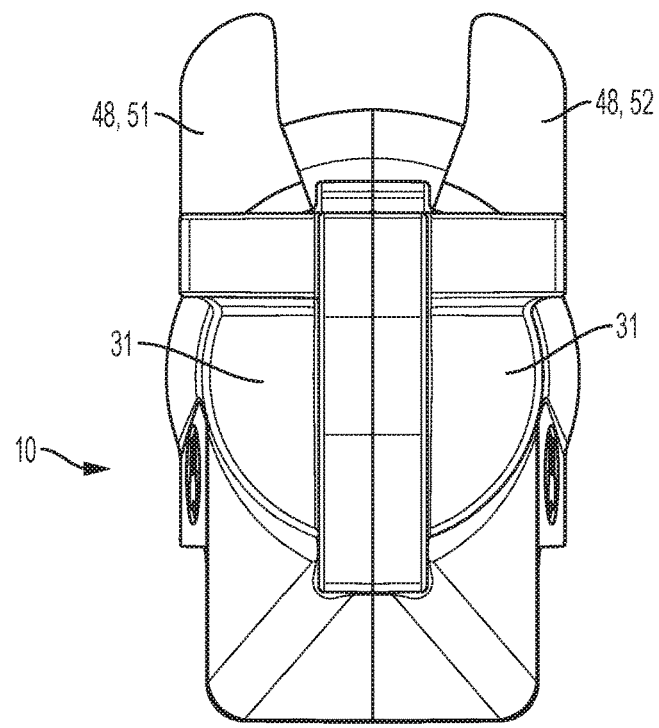
FIG. 7 is a front elevation view of the distal section of two-piece bilateral illumination attachment for dental camera.
Figure 8:
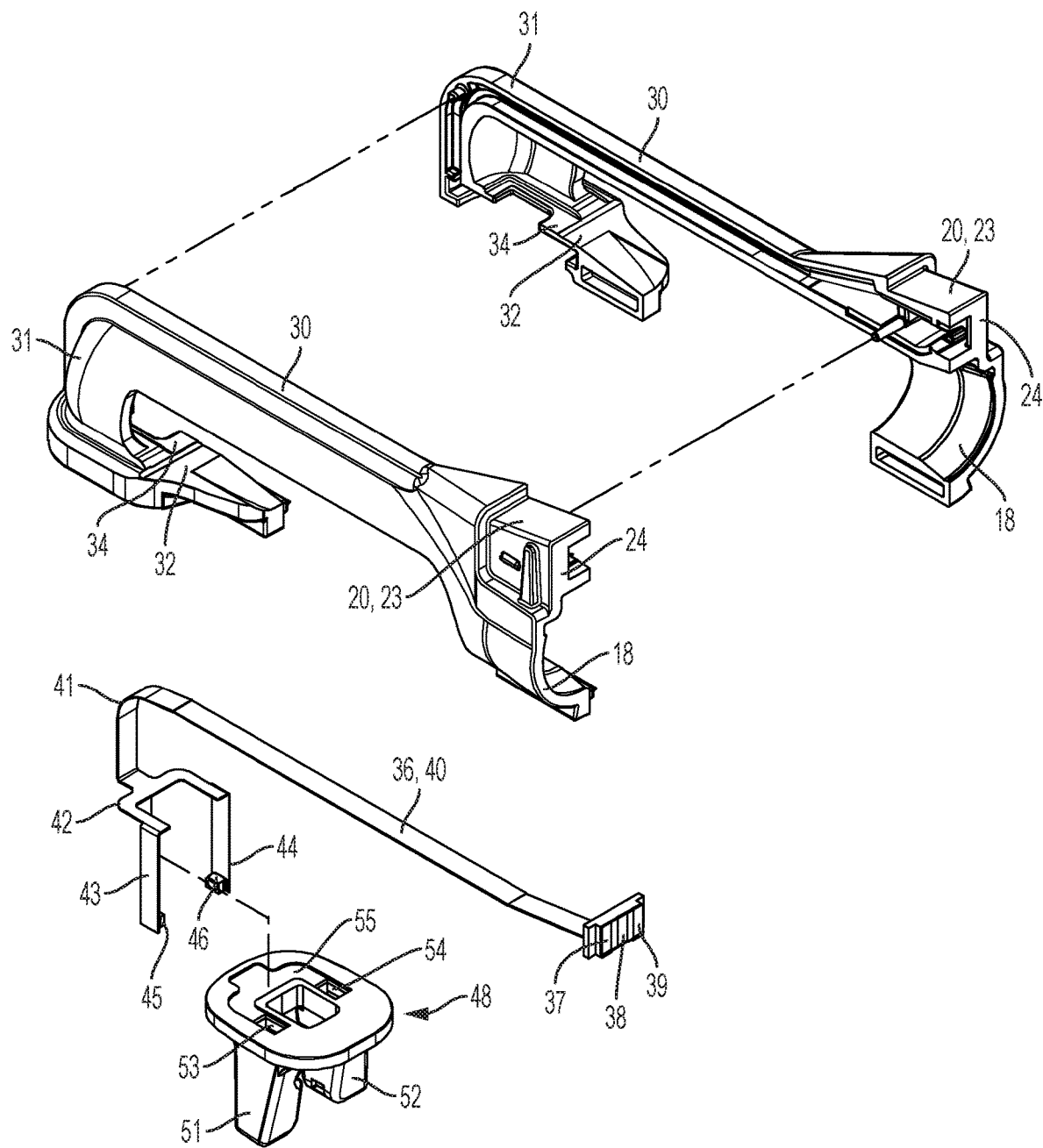
FIG. 8 is an exploded view of the distal section of two-piece bilateral illumination attachment for dental camera.
Figure 9:
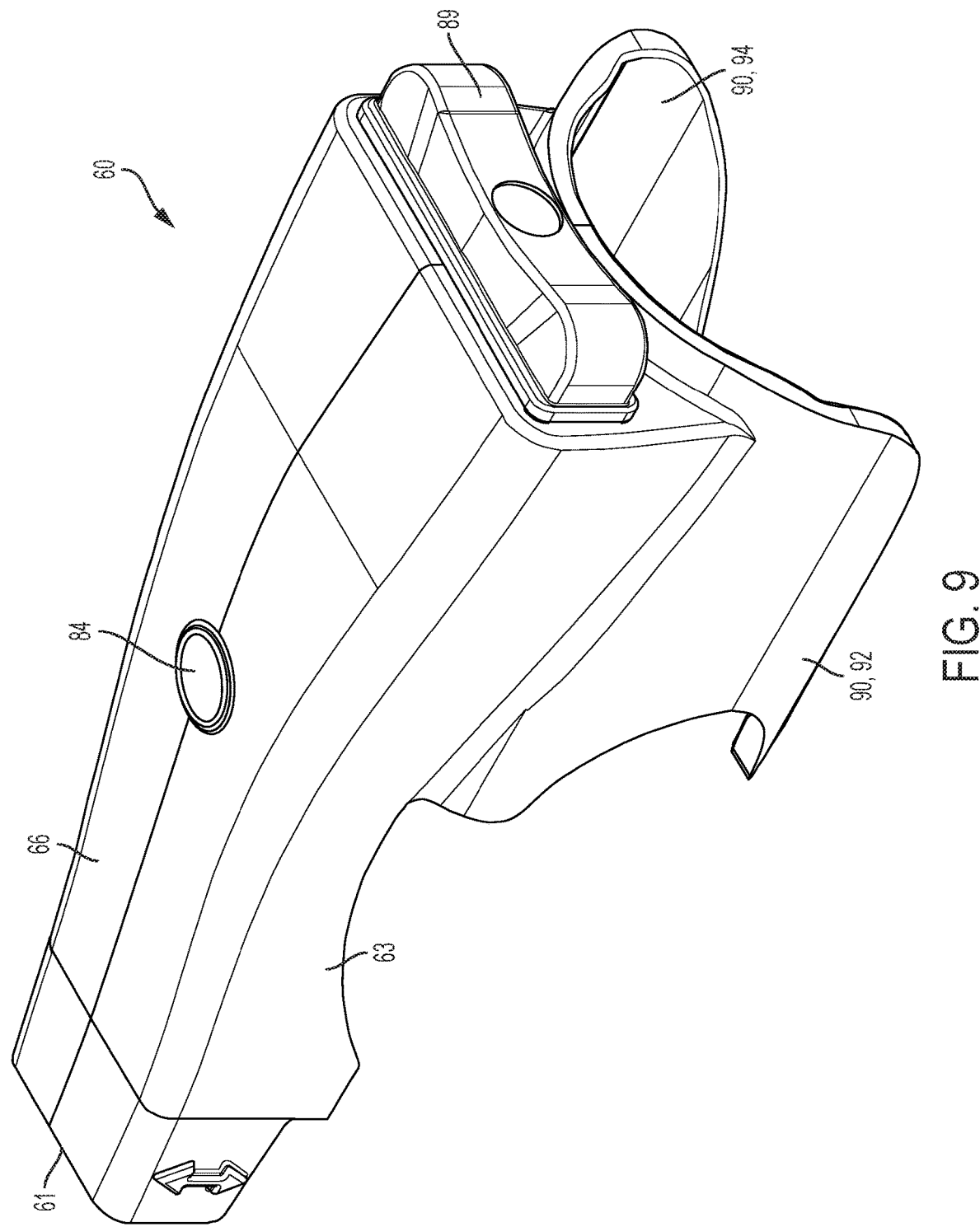
FIG. 9 is a perspective view of the proximal section of two-piece bilateral illumination attachment for dental camera.
Figure 10:
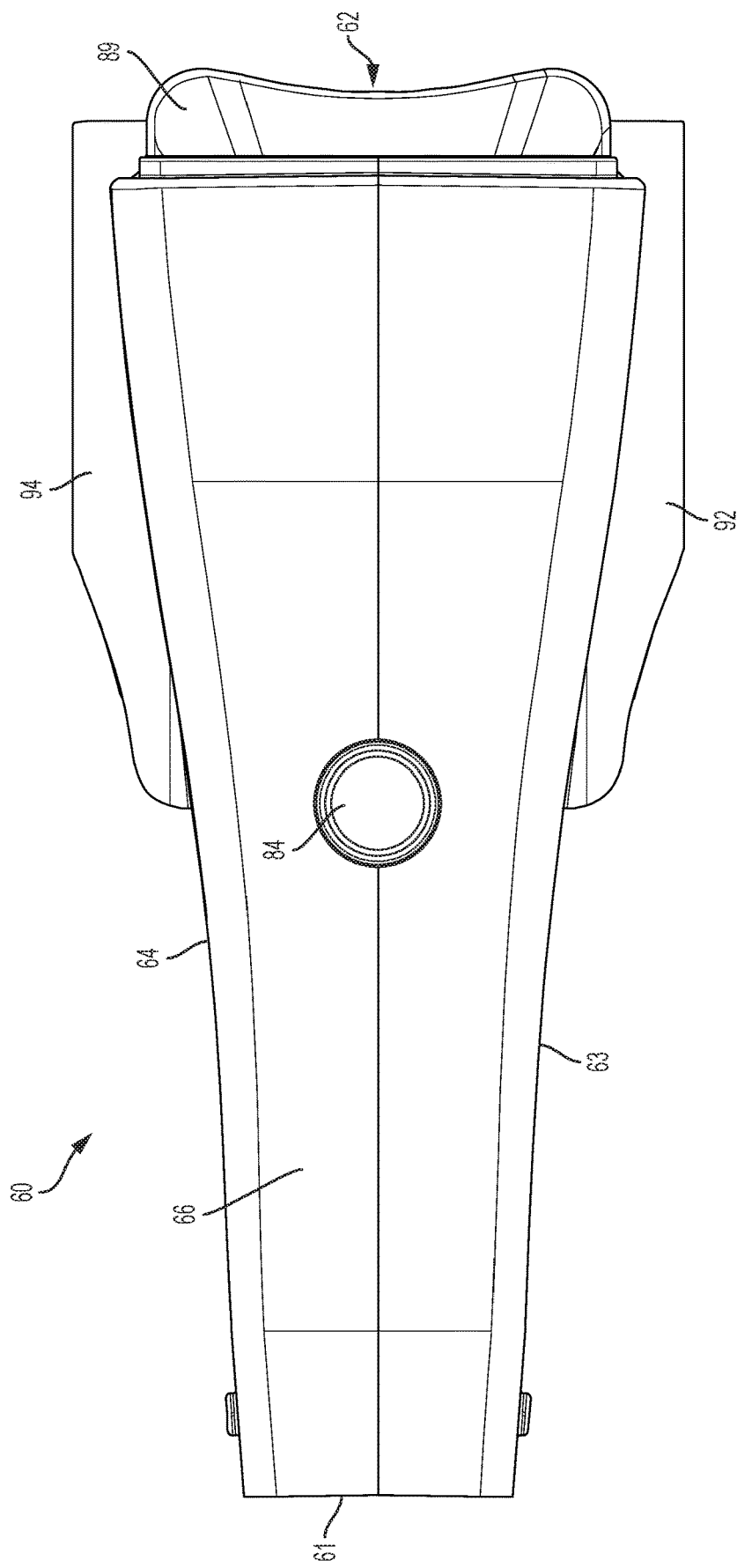
FIG. 10 is a top plan view of the proximal section of two-piece bilateral illumination attachment for dental camera.
Figure 11:
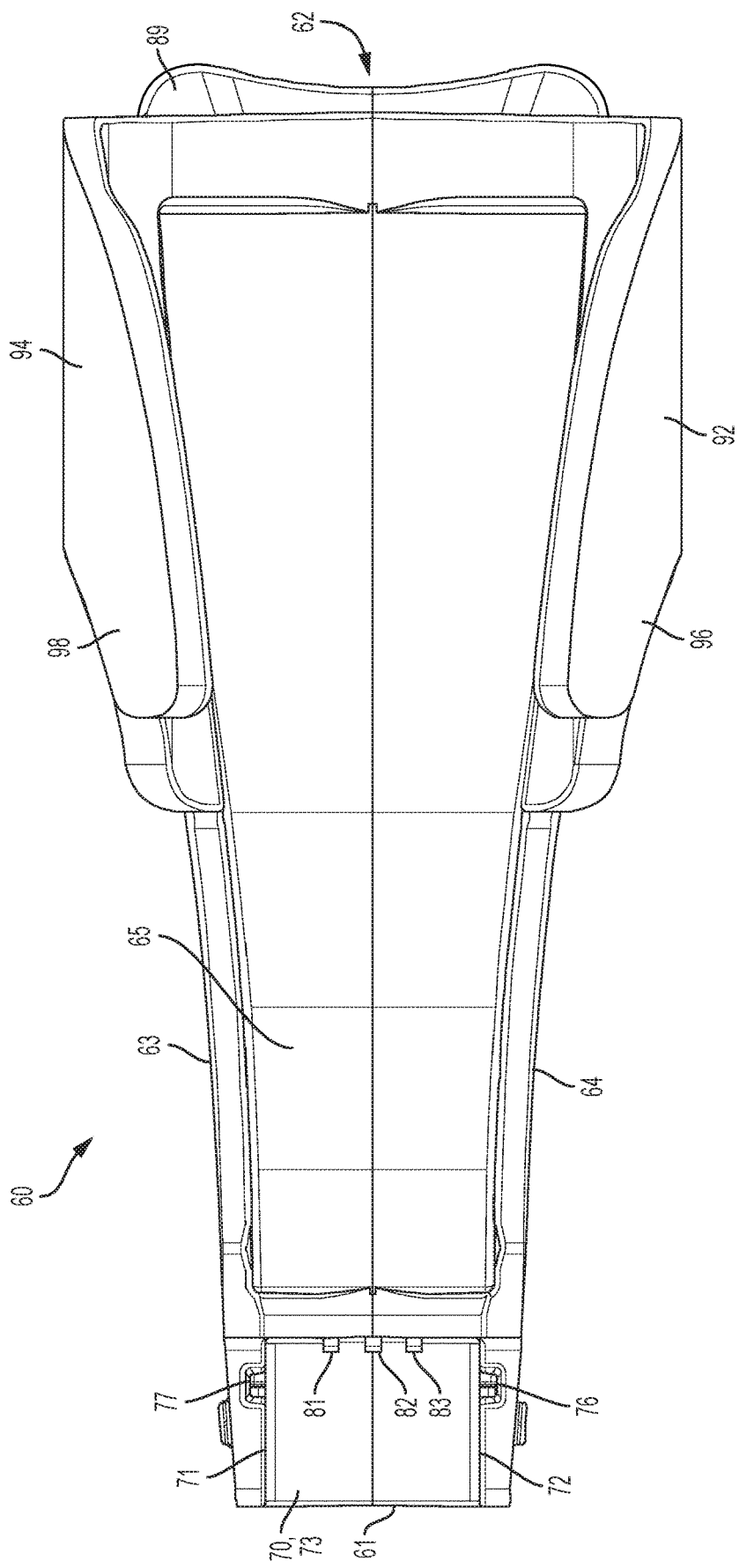
FIG. 11 is a bottom plan view of the proximal section of two-piece bilateral illumination attachment for dental camera.
Figure 12:
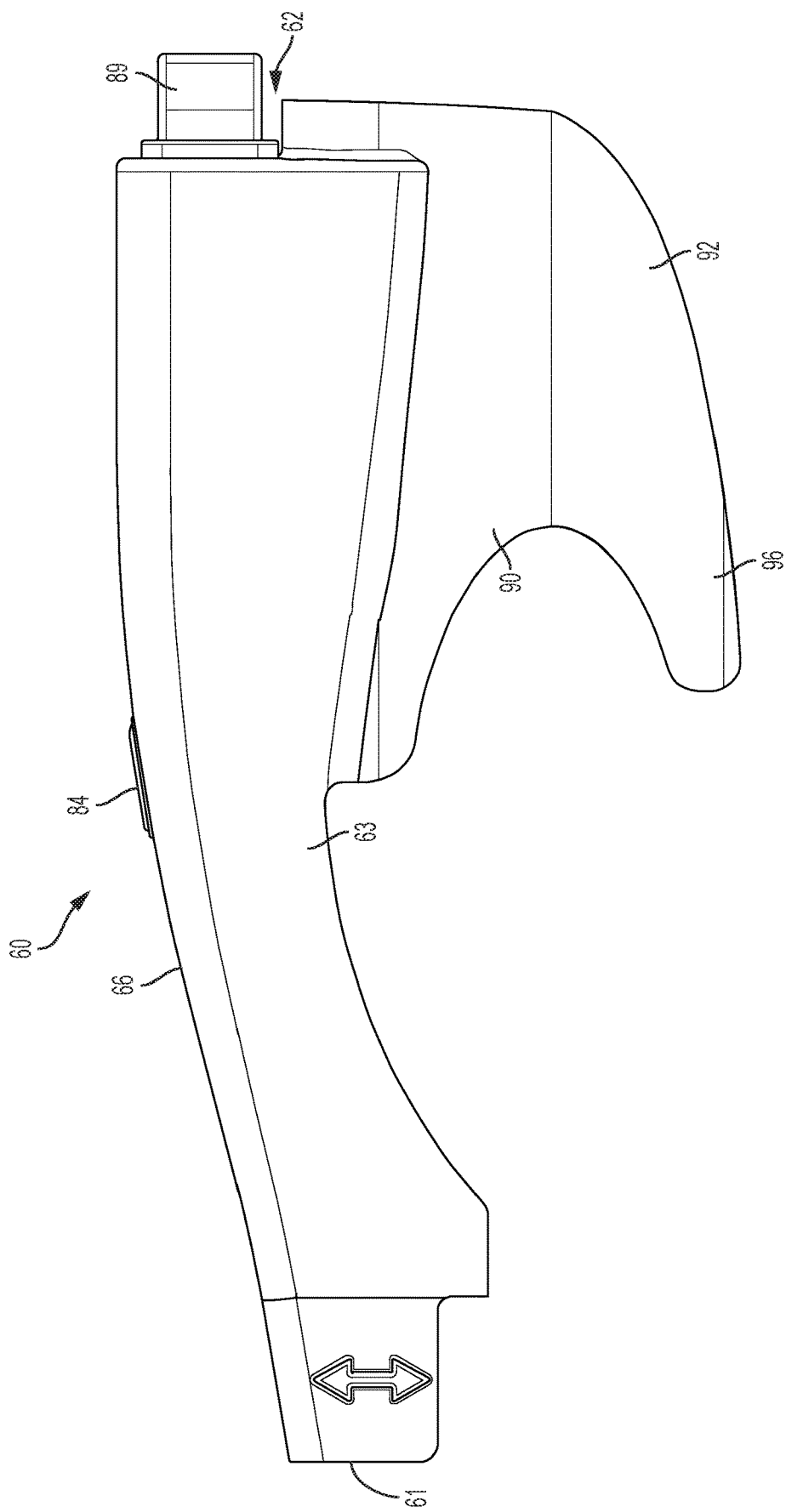
FIG. 12 is a left side elevation view of the proximal section of two-piece bilateral illumination attachment for dental camera.
Figure 13:
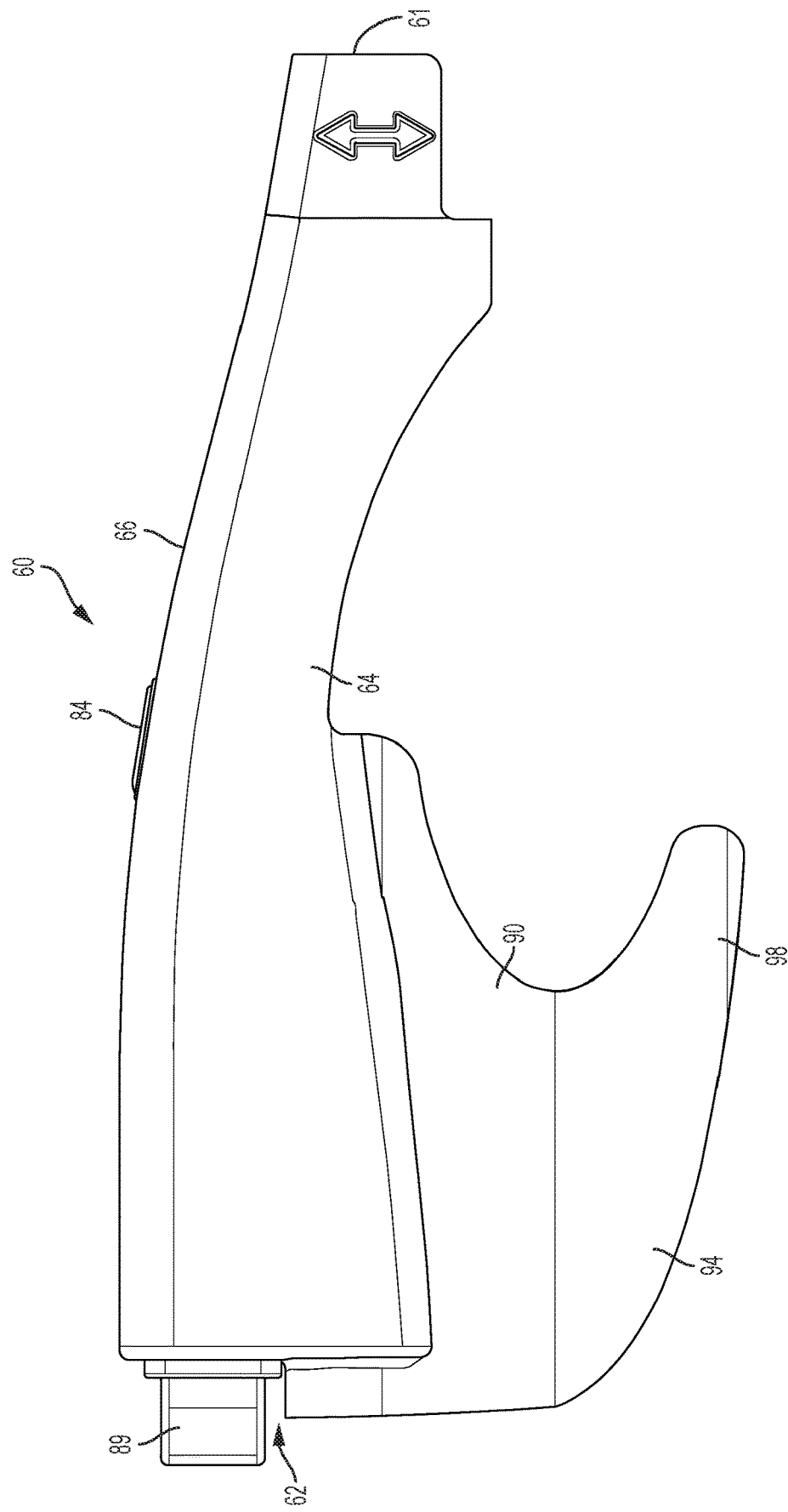
FIG. 13 is a right side elevation view of the proximal section of two-piece bilateral illumination attachment for dental camera.
Figure 14:
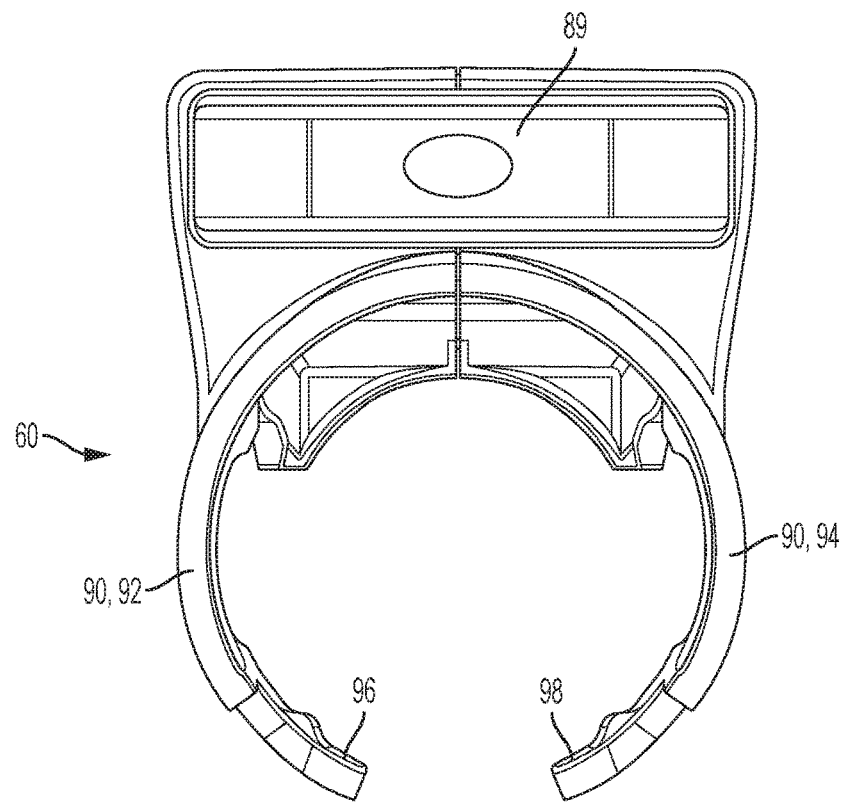
FIG. 14 is a bottom plan view of the proximal section of two-piece bilateral illumination attachment for dental camera.
Figure 15:
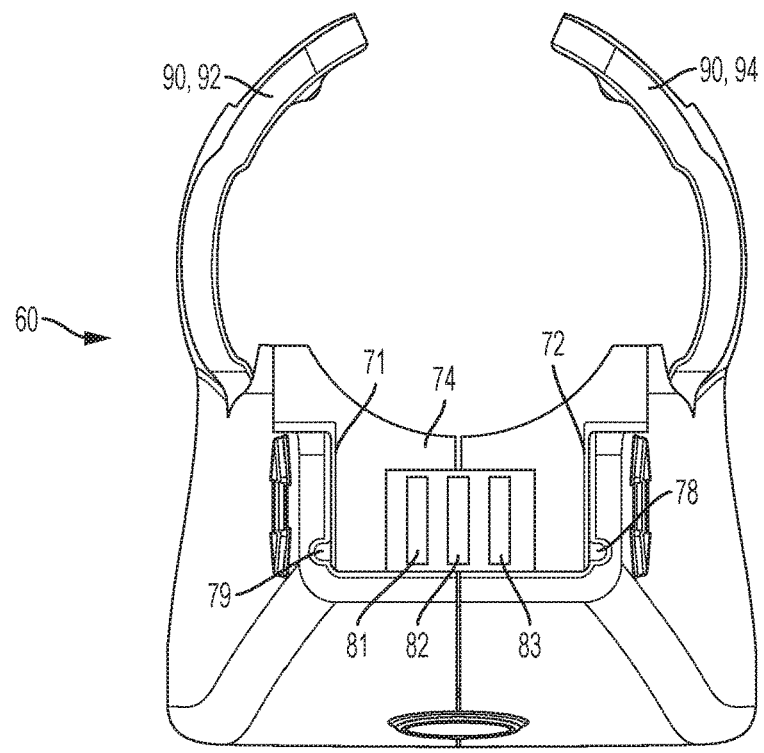
FIG. 15 is a top plan view of the proximal section of two-piece bilateral illumination attachment for dental camera.
Figure 16:
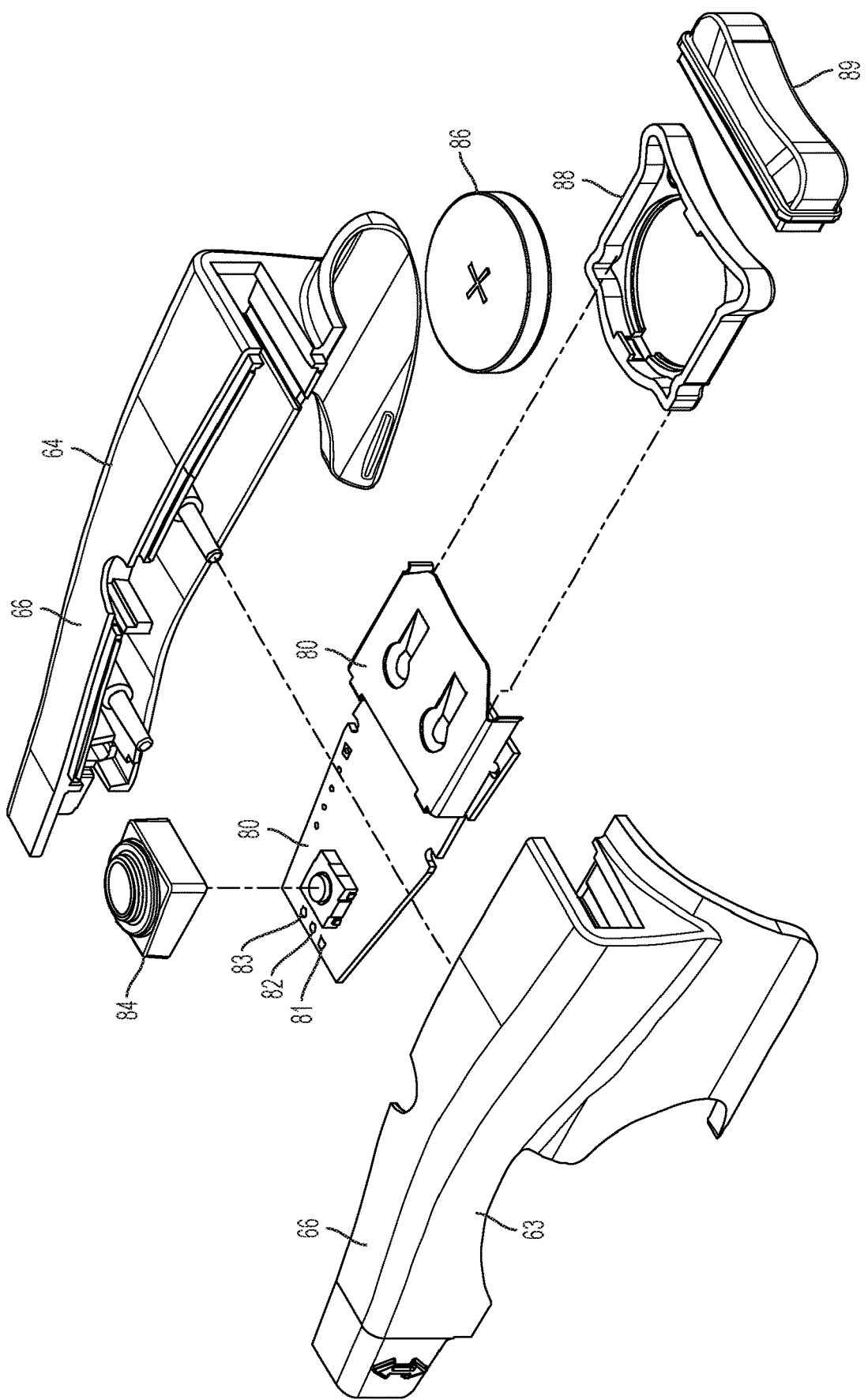
FIG. 16 is an exploded view of the proximal section of two-piece bilateral illumination attachment for dental camera.
Figure 17:
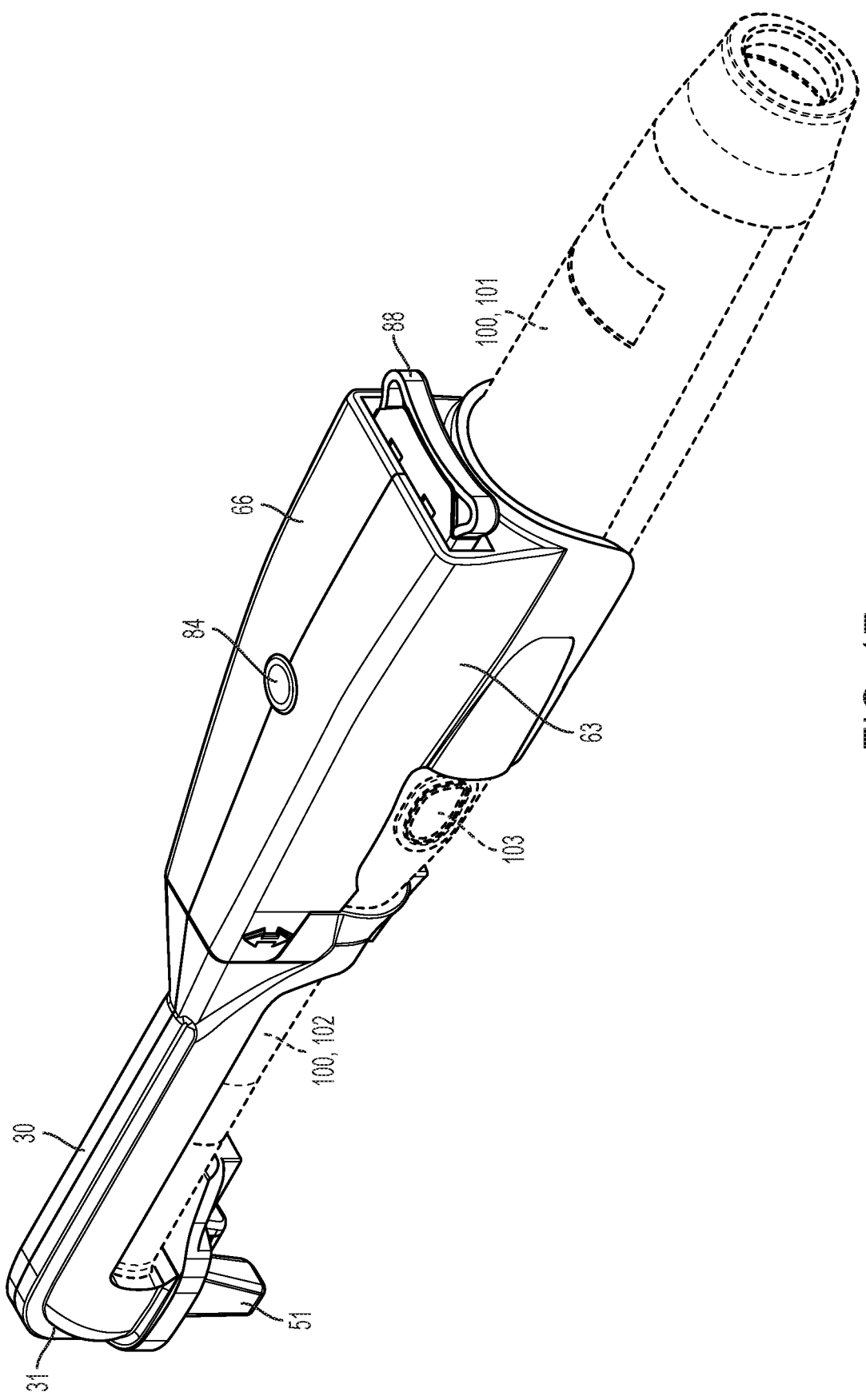
FIG. 17 is a perspective view of two-piece bilateral illumination attachment for dental camera reversibly attached to a dental camera.
Figure 18:
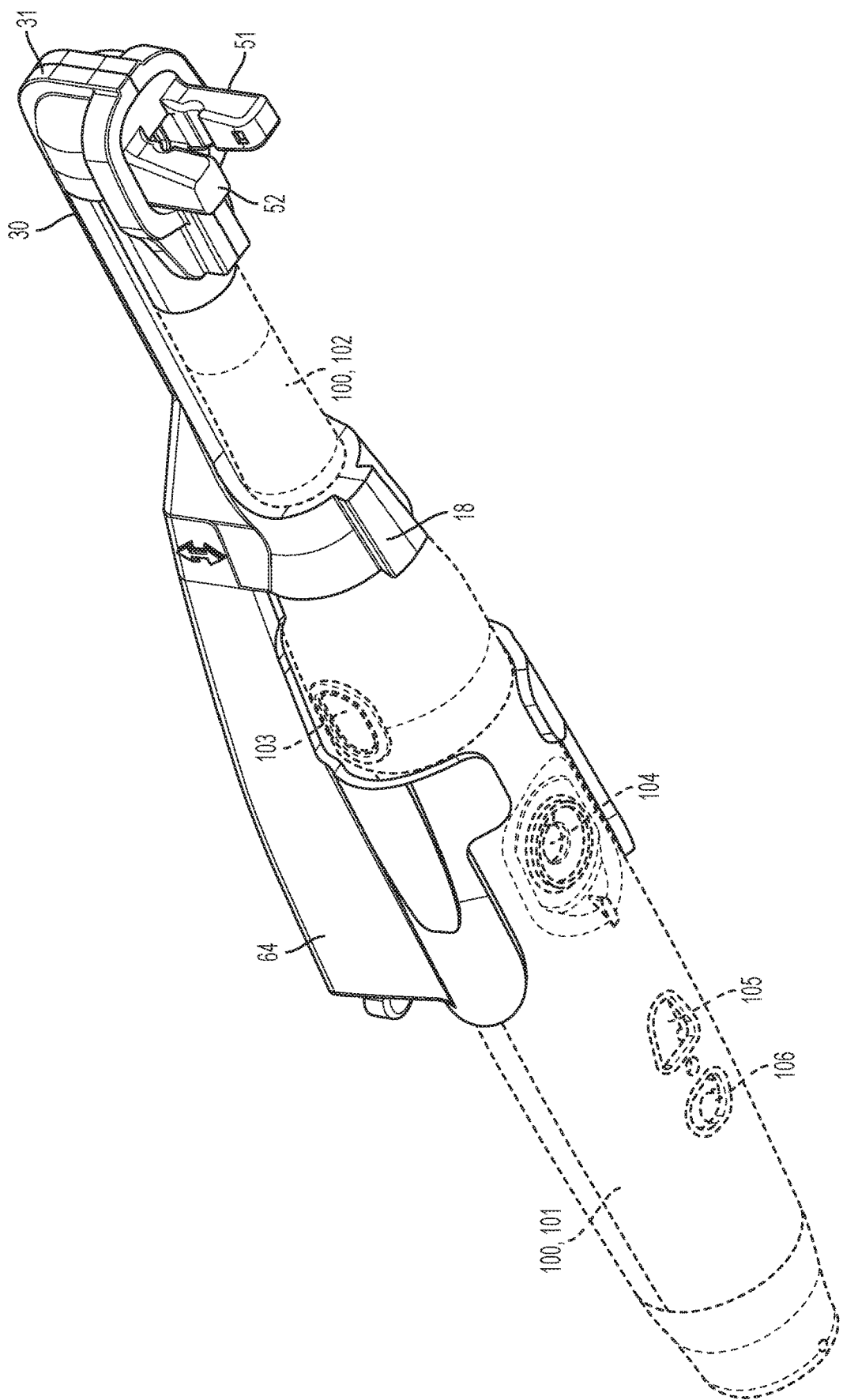
FIG. 18 is a front perspective view of two-piece bilateral illumination attachment for dental camera reversibly attached to a dental camera.

| Term | Definition |
|---|---|
| 5 | Two-Piece Bilateral Illumination Attachment for Dental Camera |
| 10 | Distal Section |
| 11 | Distal End of Distal Section |
| 12 | Proximal End of Distal Section |
| 13 | Left Side of Distal Section |
| 14 | Right Side of Distal Section |
| 15 | Concave Side of Distal Section |
| 16 | Convex Side of Distal Section |
| 18 | Locating Collar |
| 20 | Locking Key Protrusion |
| 21 | Left Surface of Locking key protrusion |
| 22 | Right Surface of Locking key protrusion |
| 23 | Crown Surface of Locking key protrusion |
| 24 | Proximal Surface of Locking key protrusion |
| 25 | Left Rail |
| 26 | Right Rail |
| 27 | Left Detent |
| 28 | Right Detent |
| 30 | Elongated Neck |
| 31 | End Cap |
| 32 | Tooth Cup Ledge |
| 33 | Camera Port in Tooth Cup Ledge |
| 34 | Tooth Cup Socket in Tooth Cup Ledge |
| 36 | Electrical Ribbon or Wiring Assembly |
| 37 | First Electrical Contact on Electrical Ribbon or Wiring Assembly |
| 38 | Second Electrical Contact on Electrical Ribbon or Wiring Assembly |
| 39 | Third Electrical Contact on Electrical Ribbon or Wiring Assembly |
| 40 | Main Run Section of Electrical Ribbon or Wiring Assembly |
| 41 | Elbow Section of Electrical Ribbon or Wiring Assembly |
| 42 | U-Member of Electrical Ribbon or Wiring Assembly |
| 43 | Left Tine Section of Electrical Ribbon or Wiring Assembly |
| 44 | Right Tine Section of Electrical Ribbon or Wiring Assembly |
| 45 | Left Light Source |
| 46 | Right Light Source |
| 48 | Dual Light Tooth Cup |
| 49 | Camera Side of Dual Light Tooth Cup |
| 50 | Tooth Side of Dual Light Tooth Cup |
| 51 | Left Arm |
| 52 | Right Arm |
| 53 | Left Arm Socket |
| 54 | Right Arm Socket |
| 55 | U-Member Recess |
| 56 | Camera Port in Tooth Cup |
| 57 | Left Crown Line |
| 58 | Right Crown Line |
| 60 | Proximal Section |
| 61 | Distal End of Proximal Section |
| 62 | Proximal End of Proximal Section |
| 63 | Left Side of Proximal Section |
| 64 | Right Side of Proximal Section |
| 65 | Concave Side of Proximal Section |
| 66 | Convex Side of Proximal Section |
| 70 | Locking Key Recess |
| 71 | Left Surface of Locking key recess |
| 72 | Right Surface of Locking key recess |
| 73 | Crown Surface of Locking key recess |
| 74 | Proximal Surface of Locking key recess |
| 76 | Right Groove |
| 77 | Left Groove |
| 78 | Right Divot |
| 79 | Left Divot |
| 80 | Circuit Board |
| 81 | First Contact on Circuit Board |
| 82 | Second Contact on Circuit Board |
| 83 | Third Contact on Circuit Board |

-continued

DEFINITION LIST

| Term | Definition |
|---|---|
| 84 | On Off Switch |
| 86 | Battery |
| 88 | Battery Tray |
| 89 | Battery Lid |
| 90 | Half Socket |
| 92 | Left Wing |
| 94 | Right Wing |
| 96 | Left Wing Tip |
| 98 | Right Wing Tip |
| 100 | Dental Camera |
| 101 | Larger Diameter End or Proximal End of Dental Camera |
| 102 | Smaller Diameter End or Distal End of Dental Camera |
| 103 | Capture Switch on Dental Camera |
| 104 | Focus Wheel on Dental Camera |
| 105 | Light On Off Switch on Dental Camera |
| 106 | On Off Power Switch on Dental Camera |

DETAILED DESCRIPTION OF THE INVENTION

Two-piece bilateral illumination attachment for dental camera 5 is reversibly attachable to a dental camera 100. A dental camera 100 is a camera that is used to take pictures or images of the interior of a patient's mouth and the exterior of a patient's face. Dental cameras 100 are typically used to take a picture or capture an image of a problem tooth in order to show the patient and for record keeping purposes. A dental camera 100 is also known as an intraoral camera. All dental cameras 100 have a tapered cylindrical exterior shape with a larger diameter end 101 and a smaller diameter end 102 as depicted. The larger diameter end 101 is the gripping end where the operator grips or holds this end to operate the dental camera 100. The larger diameter end 101 of dental camera 100 is the proximal end of dental camera 100. The smaller diameter end 102 of dental camera 100 is the distal end of dental camera 100. The smaller diameter end 102 of dental camera 100 has a distal tip with an image sensor and a light source located thereon. The distal tip with image sensor and light source is placed into the interior of the patient's mouth when using a dental camera 100 to take pictures or images of the interior of a patient's mouth. There is a smooth taper between the larger diameter end 101 and the smaller diameter end 102 on the exterior surface of dental camera 100. Dental camera 100 has a capture switch 103, which is the button used to take pictures or capture images of a tooth. Dental camera 100 has a focus wheel 104, which is used to adjust focus of the image. Dental camera 100 has a light on off switch 105, which is the button used to control the light source or flash on dental camera 100. Dental camera 100 has an on off power switch 106, which is the button turn the dental camera 100 on and off. There are many different brands of dental camera 100 in the market place where each brand may have its own specific tapered cylindrical shape, however, most, if not all, brands have a larger diameter end 101 with a smooth tapered mid-section leading to a smaller diameter end 102 as described above. Two-piece bilateral illumination attachment for dental camera 5 is reversibly attachable to any brand or model of dental camera 100 with a larger diameter end 101 and smooth tapered mid-section leading to a smaller diameter end 102. Since the exact dimensions of the larger diameter end 101 and the smaller diameter end 102 may differ for each model of dental cameras 100 may differ, a specifically sized two-piece bilateral illumination attachment for dental camera 5 may be required for each specific model of dental camera 100.

Two-piece bilateral illumination attachment for dental camera 5 comprises: a distal section 10 and a proximal section 60. The primary purpose of the two-piece design is to allow the distal section 10 to be separated from the proximal section 60 and sterilized separately from the proximal section 60 without damaging the electronics and battery in the proximal section. Distal section 10 is reversibly attachable to proximal section 60 and vice versa. Reversible attachment is such that electrical continuity is created between the distal section 10 and the proximal section 60 when properly attached to each other. Reversible attachment is such that a strong rigid connection occurs between the distal section 10 and the proximal section 60 when attached to each other. Strong rigid attachment is primarily accomplished by a locking key protrusion 20 on the distal section 10 that mates with a locking key recess 70 on proximal section 60. Locking key protrusion 20 is reversibly attachable to locking key recess 70 and vice versa. When the distal section 10 and a proximal section 60 are properly attached together, a specially shaped structural member is formed that makes a slip-fit, press-fit, or snap-fit over the exterior surface of a dental camera 100.

Distal section 10 may be made from any known material that is rigid and capable of being sterilized by heat or chemical means. Distal section 10 and proximal section 60 may be made from steel, metal, composite, plastic, polymer, carbon fiber, fiberglass, epoxy, or similar. In best mode, as depicted, distal section 10 and proximal section 60 each have a two-piece hollow clamshell structure. As depicted, there is a longitudinal seam running completely around distal section 10 and proximal section 60 defining the two pieces of the clamshell structure. In the hollow clamshell structure, there are two pieces or halves that press together and rigidly attach together like a clamshell. The hollow clamshell design makes for easier production and assembly of distal section 10 where an electrical ribbon or wiring assembly 36 and a dual light tooth cup 48 are installed between the two hollow clamshell pieces prior to pressing them together or rigidly attaching them together to form the proximal section 60. The two pieces or halves may be rigidly attached together by any known means such as glue, adhesive, epoxy, welding, sonic welding, soldering, press-fit, clips, or similar. The hollow clamshell design makes for easier production and assembly of proximal section 60 where a circuit board 80, a battery 86, and other items are installed between the two hollow clamshell pieces prior to pressing them together or rigidly attaching them together to form the proximal section 60. The two pieces or halves may be rigidly attached together by any known means such as glue, adhesive, epoxy, welding, sonic welding, soldering, press-fit, clips, or similar.

Distal section 10 is a rigid oblong structural member with a distal end 11, a proximal end 12, a left side 13, a right side 14, a concave side 15, a convex side 16, and a longitudinal axis. Distal end 11 is the end of distal section 10 that is farthest from the operator during operation of two-piece bilateral illumination attachment for dental camera 5. Proximal end 12 is the end of distal section 10 that is closest to the operator during operation of two-piece bilateral illumination attachment for dental camera 5. Concave side 15 has a general concave shape and a concave surface. Concave side 15 is the side of distal section 10 that is faces or is adjacent to dental camera 100 when two-piece bilateral illumination attachment for dental camera 5 is properly attached to dental camera 100. Convex side 16 has a general convex shape and a convex surface. Convex side 16 is the side of distal section 10 that is opposite of dental camera 100 when two-piece bilateral illumination attachment for dental camera 5 is properly attached to dental camera 100. Left side 13 is located on the operator's left side during operation of two-piece bilateral illumination attachment for dental camera 5. Right side 14 is located on the operator's right side during operation of two-piece bilateral illumination attachment for dental camera 5. Concave side 15 is specially sized and shaped to make a slip-fit, press-fit, or snap-fit onto the smaller diameter end 102 of dental camera 100. This special shape includes: a locating collar 18, a locking key protrusion 20, an elongated neck 30, an end cap 31, and a tooth cup ledge 32.

Distal section 10 further comprises: a locating collar 18 and locking key protrusion 20. Locating collar 18 and locking key protrusion 20 are located on proximal end 12 of distal section 10. Locating collar 18 and locking key protrusion 20 are adjacent to each other. Locking key protrusion 20 is on the convex side 16 of proximal end 12 while locating collar 18 is on the concave side 15 of proximal end 12 as depicted.

Locating collar 18 is a rigid tapered cylindrical member with open ends. Locating collar 18 has a distal end, a proximal end, a tapered side, and a longitudinal axis. Distal end has a circular opening with an inner diameter. Proximal end has a circular opening with an inner diameter. The inner diameter of distal end is smaller than that of proximal end. Tapered side is tapered with a smooth tapered inner diameter that varies from distal end to proximal end to yield a smooth taper. The inner diameter of tapered side is sized and shaped to make a slip-fit or press-fit over the tapered outer diameter of dental camera 100. The longitudinal axis of locating collar 18 is parallel with that of distal section 10. A portion of the tapered side of locating collar 18 is contiguous with or rigidly attached to locking key protrusion 20. The longitudinal axis of locating collar 18 is coincident with that of elongated neck 30.

Locking key protrusion 20 is a rigid rectangular cuboid-shaped, cube-shaped protrusion, or key-shaped protrusion on the convex side 16 of distal section 10 at the proximal end 12 of distal section 10 as depicted. Locking key protrusion 20 mates with a locking key recess 70 on proximal section 60 when distal section 10 is properly attached to proximal section 60. Locking key protrusion 20 has a left surface 21, a right surface 22, a crown surface 23, and a proximal surface 24. Left surface 21 is located on the operator's left side during operation of two-piece bilateral illumination attachment for dental camera 5. Right surface 22 is located on the operator's right side during operation of two-piece bilateral illumination attachment for dental camera 5. Crown surface 23 is located on the convex side 16 of distal section 10. Proximal surface 24 is located on the proximal end 12 of distal section 10. Left surface 21, right surface 22, crown surface 23, and proximal surface 24 are each essentially planer members. Left surface 21, right surface 22, crown surface 23, and proximal surface 24 make up four sides of the rectangular cuboid-shaped or cube-shaped protrusion that is locking key protrusion 20. The other two sides of the rectangular cuboid-shaped or cube-shaped protrusion are integrated within distal section 10 where an elongated neck 30 is contiguous with locking key protrusion 20 at the distal end of locking key protrusion and locating collar 18 is contiguous with locking key protrusion 20 on the concave side of locking key protrusion 20.

Locking key protrusion 20 may further comprise: a left rail 25 and a right rail 26. Left rail 25 is a rail or linear protrusion on the left surface 21 of locking key protrusion 20. Left rail 25 has a length, a width, a height, and a longitudinal axis. The longitudinal axis of left rail 25 may run parallel or perpendicular to that of distal section 10. Left rail 25 is sized to make a slip-fit with a left groove 77 on locking key recess 70. Left rail 25 slides within left groove 77, along the longitudinal axis of left rail 25, when the distal section 10 is being attached to and/or detached from proximal section 60. Right rail 26 is a rail or linear protrusion on the right surface 22 of locking key protrusion 20. Right rail 26 has a length, a width, a height, and a longitudinal axis. The longitudinal axis of left rail 25 is parallel with that of right rail 26. Right rail 26 is sized to make a slip-fit with a right groove 76 on locking key recess 70. Right rail 26 slides within right groove 76, along the longitudinal axis of right rail 26, when the distal section 10 is being attached to and/or detached from proximal section 60.

Left and right rails 25,26 along with left and right grooves 77,76 function to guide and align locking key protrusion 20 properly within locking key recess 70 during attachment and/or detachment of distal section 10 and proximal section 60. Left and right rails 25,26 along with left and right grooves 77,76 also function to guide and align first, second, and third electrical contacts 37,38,39 properly to contact first, second, and third contacts 81,82,83 during attachment and/or detachment of distal section 10 and proximal section 60. When distal section 10 is properly attached to proximal section 60, there is electrical continuity between first electrical contact 37 and first contact 81. When distal section 10 is properly attached to proximal section 60, there is electrical continuity between second electrical contact 38 and second contact 82. When distal section 10 is properly attached to proximal section 60, there is electrical continuity between third electrical contact 39 and third contact 83.

Locking key protrusion 20 may further comprise: a left detent 27 and a right detent 28. Left detent 27 and right detent 28 are each a detent, catch, dog, spring-operated ball, or flexible protrusion. Right detent 28 is on the right surface 22 of locking key protrusion 20. Right detent 28 nests within or catches within a right divot 78 on locking key recess 70 when distal section 10 is properly attached to proximal section 60. Left detent 27 is on the left surface 21 of locking key protrusion 20. Left detent 27 nests within or catches within a left divot 79 on locking key recess 70 when distal section 10 is properly attached to proximal section 60. Left and right detents 27,28 function with left and right divots 79,78 to rigidly lock and hold the distal section 10 onto the proximal section 60 when the two sections are properly attached or snapped together.

Distal section 10 further comprises an elongated neck 30. Elongated neck 30 is an elongated rigid structural member. Elongated neck 30 has a distal end, proximal end, left side, right side, concave side, convex side, a length, and a longitudinal axis. The proximal end of elongated neck 30 is adjacent to and contiguous with or rigidly attached the distal end of locating collar 18. Left side is located on the operator's left side when facing the convex side. Right side is located on the operator's right side when facing the convex side. Concave side of elongated neck 30 is a partial cylindrical surface with an inner diameter. The inner diameter of concave side is sized and shaped to make a slip-fit or press-fit over the outer diameter of the smaller diameter end 102 of dental camera 100. The inner diameter of concave side is equivalent to that of the distal end of locating collar 18 thereby making a smooth transition of inner diameter between the locating collar 18 and the elongated neck 30. Concave side of elongated neck 30 is a partial cylindrical surface because most of the side of the hollow cylindrical member is void or removed to yield an open space. When two-piece bilateral illumination attachment for dental camera 5 is attached to dental camera 100, the concave side of elongated neck 30 covers about 90 to 180 degrees of the smaller diameter end 102 of dental camera 100 when attached thereto. Thus, the concave side of elongated neck 30 wraps around the smaller diameter end 102 of dental camera 100 about 90 to 180 degrees when attached thereto.

Both ends of rigid hollow partial cylindrical member are void or open. The voids or open ends allow for easier insertion, attachment, detachment, and removal of the two-piece bilateral illumination attachment for dental camera 5 onto the dental camera 100. The length of elongated neck 30 is about 70-95 percent of the length of distal section 10. The longitudinal axis of elongated neck 30 is parallel with that of distal section 10. The longitudinal axis of elongated neck 30 is parallel with that of locating collar 18.

The interior of elongated neck 30 has a longitudinal wire conduit running along the entire length of elongated neck 30. Longitudinal wire conduit is an internal channel or cavity running from locking key protrusion 20 to a tooth cup ledge 32. Longitudinal wire conduit has a distal end and a proximal end. The distal end of longitudinal wire conduit connects with tooth cup ledge 32. The proximal end of longitudinal wire conduit connects with locking key protrusion 20. Longitudinal wire conduit is a conduit for an electrical ribbon or wiring assembly 36.

Distal section 10 further comprises an electrical ribbon or wiring assembly 36. Electrical ribbon or wiring assembly 36 is an assembly of two or more electrically conductive members. Electrically conductive members are each capable of transmitting electrical signals or electric current from end to end. Electrical ribbon or wiring assembly 36 has a proximal end and a distal end. Each of the two or more electrically conductive members has an electrical connector attached to the proximal end and a light source attached to the distal end. Electrical ribbon or wiring assembly 36 may be an assembly or harness of wires or strips. Electrical ribbon or wiring assembly 36 may be a printed circuit board with conductor paths printed on the circuit board or a series of printed circuit boards with conductor paths printed on the circuit boards. Electrical ribbon or wiring assembly 36 is sterilizeable by heat or chemical means. Electrical ribbon or wiring assembly 36 may be made from any known material that is sterilizeable and capable of carrying and electrical signal. Electrically conductive members may be made from copper, gold, steel, metal, composite, plastic, polymer, carbon fiber, or similar. In the best modes, electrical ribbon or wiring assembly 36 is a rigid or semi-rigid assembly, which allows for easier assembly and manufacturing of two-piece bilateral illumination attachment for dental camera 5.

Electrical ribbon or wiring assembly 36 comprises: a first electrical contact 37, a second electrical contact 38, a main run section 40, an elbow section 41, a U-member 42, a left tine section 43, a right tine section 44, a left light source 45, a right light source 46, a first electrically conductive member, and a second electrically conductive member. First electrical contact 37 is a rigid planar member that is electrically conductive. Second electrical contact 38 is a rigid planar member that is electrically conductive. First and second electrical contacts 37,38 may be made from copper, gold, steel, metal, composite, plastic, polymer, carbon fiber, or similar. First and second electrically conductive members are each electrically conductive members with a proximal end and a distal end. First and second electrically conductive members may be made from copper, gold, steel, metal, composite, plastic, polymer, carbon fiber, or similar. First and second conductive member are each isolated and electrically insulated from all other conductive members. The proximal end of first conductive member is connected to and has electrical continuity with first electrical contact 37. The proximal end of second conductive member is connected to and has electrical continuity with second electrical contact 38. First and second electrical contacts 37,38 are attached to the proximal end of main run section 40. Main run section 40 is an elongated member with a proximal end, a distal end, and a longitudinal axis. First and second electrically conductive members run from the first and second electrical contacts 37,38 at the proximal end of main run section 40 and pass through the distal end of main run section 40. In best mode, main run section 40 is rigid. Elbow section 41 is a 90-degree bend or elbow with a proximal end and a distal end. First and second electrically conductive members pass in through the proximal end of elbow section 41 and out through the distal end of elbow section 41. The proximal end of elbow section 41 is rigid attached to the distal end of main run section 40. In best mode, elbow section 41 is rigid. U-member 42 is an inverted U-shaped member with top side, a left leg, and a right leg. First electrically conductive member passes in through the top side of U-member 42 and down the left leg of U-member 42. Second electrically conductive member passes in through the top side of U-member 42 and down the right leg of U-member 42. The top side of U-member 42 is attached to the distal end of main run section 40. The bottom of left leg of U-member 42 is attached to the proximal end of left tine section 43. The bottom of right leg of U-member 42 is attached to the proximal end of right tine section 44. In best mode, U-member 42 is rigid. Left tine section 43 is an elongated member with proximal end and a distal end. First electrically conductive member passes in through the proximal end of left tine section 43 to terminate at the distal end of left tine section 43. In best mode, left tine section 43 is rigid. Right tine section 44 is an elongated member with proximal end and a distal end. Second electrically conductive member passes in through the proximal end of right tine section 44 to terminate at the distal end of right tine section 44. In best mode, right tine section 44 is rigid. Left light source 45 is a light source attached to the distal end of left tine section 43. Right light source 46 is a light source attached to the distal end of right tine section 44. Left light source 45 is connected to and has electrical continuity with first electrically conductive member. Right light source 46 is connected to and has electrical continuity with second electrically conductive member. Left and right light sources 45,46 are each an electric light source. Any known type and/or color of electrical light source may be used such as incandescent, fluorescent, halogen, CFL, LED, or similar. In best mode, left and right light sources 45,46 are each white LED lights.

Electrical ribbon or wiring assembly 36 is a one-piece assembly. First and second electrically conductive members pass entirely through the electrical ribbon or wiring assembly 36 from proximal end to distal end. There is electrical continuity between first electrical contact 37 and left light source 45. There is electrical continuity between second electrical contact 38 and right light source 46. When electrical ribbon or wiring assembly 36 is properly installed or assembled within distal section 10, first electrical contact 37 and second electrical contact 38 are each located on the proximal surface 24 of locking key protrusion 20 or alternately each located on the crown surface 23 of locking key protrusion 20. In best mode, first electrical contact 37 and second electrical contact 38 are each located on the proximal surface 24, as depicted. First electrical contact 37 functions as a direct current power source or ground source to left light source 45. Second electrical contact 38 function as a direct current power source or ground source to right light source 46. In t, this mode, there is a cross-tine electrically conductive member that connects the left light source 46 to the right light source 46 to function as a direct current power source or ground source to both lights 45,46. In best mode, left light source 45 and right light source 46 are connected in parallel to a direct current power source or ground source so that so that the on off switch 84 controls both lights simultaneously.

In order to control left and right light sources 45,46 individually, a third electrical contact 39 and a third electrically conductive member are required. Electrical ribbon or wiring assembly 36 may further comprise a third electrical contact 39 and a third electrically conductive member. Third electrical contact 39 and third electrically conductive member are not required for proper functioning of two-piece bilateral illumination attachment for dental camera 5 but may be optionally added. Third electrical contact 39 is located adjacent to second electrical contact 38 on the proximal surface 24 or the crown surface 23 of locking key protrusion 20. Third electrically conductive member is located adjacent to first and second electrically conductive members. Third electrical contact 39 has electrical continuity with both the left light source 45 and the right light source 46. Third electrically conductive member runs along the entire length of electrical ribbon or wiring assembly 36 along side of first and second electrically conductive members. Third electrical contact 39 and third electrically conductive member allow individual control over the left light source 45 and the right light source 46. Third electrical contact 39 may be made from copper, gold, steel, metal, composite, plastic, polymer, carbon fiber, or similar. In this mode, left light source 45 and right light source 46 are each individually connected to battery 86 so that the on off switch 84 may switch each light on and off individually.

Distal section 10 further comprises an end cap 31. End cap 31 is a specially shaped rigid structural member that functions as the point of attachment to and detachment from the distal tip of dental camera 100. End cap 31 is reversibly attachable over the distal tip of dental camera 100. End cap 31 is rigid cup-shaped, socket-shaped, or U-shaped member where the cup, socket, or U shape is reversibly attachable over the distal tip of dental camera 100. End cap 31 has a closed distal end and an open proximal end. The distal end of end cap 31 is the closed end or bottom of the cup, socket, or U shape. The proximal end of end cap 31 is the open end or top of the cup, socket, or U shape. The distal end of elongated neck 30 is contiguous with or rigidly attached a point on the open proximal end of end cap 31.

Distal section 10 further comprises a tooth cup ledge 32. Tooth cup ledge 32 is a rigid planar member. Tooth cup ledge 32 has a distal end, a proximal end, a camera side surface, and a tooth side surface. Distal end is the end of tooth cup ledge 32 that is furthest from the operator during operation of two-piece bilateral illumination attachment for dental camera 5. Proximal end is the end of tooth cup ledge 32 that is closest to the operator during operation of two-piece bilateral illumination attachment for dental camera 5. The camera side surface of tooth cup ledge 32 is contiguous with or rigidly attached to the side of or proximal open end of end cap 31. The camera side surface faces or is adjacent to dental camera 100 when two-piece bilateral illumination attachment for dental camera 5 is attached to dental camera

100. Camera side surface of tooth cup ledge 32 is sized and shaped to make a slip-fit or press-fit with outer surface of the image sensor and the outer surface of the light on the distal end of dental camera 100. The tooth side surface of tooth cup ledge 32 faces or is adjacent to the patient's tooth during use of the two-piece bilateral illumination attachment for dental camera 5. Tooth cup ledge 32 further comprises: a camera port 35 and tooth cup socket 34. Camera port 33 is an open space, void, or aperture in tooth cup ledge 32 to allow for the image sensor on the distal end of dental camera 100 to have an open path or clear field of view of the tooth during use of the two-piece bilateral illumination attachment for dental camera 5 for sub-enamel illumination or bilateral illumination of the tooth. An open path or clear field of view between the image sensor and the tooth is required to allow the image sensor on dental camera 100 to capture an image or take a picture of the tooth during sub-enamel illumination or bilateral illumination of the tooth. Tooth cup socket 34 is a specially shaped socket, recess, or depression in the tooth side surface of tooth cup ledge 32. Tooth cup socket 34 is sized and shaped to accept a dual light tooth cup 48. Dual light tooth cup 48 is installed into tooth cup socket 34. Dual light tooth cup 48 is rigidly attached to tooth cup socket 34. Tooth cup socket 34 functions to help secure and rigidly attach dual light tooth cup 48 to tooth cup ledge and to distal section 10.

Dual light tooth cup 48 is inserted into a patient's mouth during use of the two-piece bilateral illumination attachment for dental camera 5. Dual light tooth cup 48 is placed over the coronal surface or crown of the tooth where the left light source 45 and the right light source 46 straddle the tooth and project light directly towards each other, into the interior of the tooth in order to effect or yield sub-enamel illumination or bilateral illumination of the tooth so that the image sensor on the distal tip of dental camera 100 may then take or capture an image or picture from the light projected out of the coronal surface or crown of the tooth of interest.

Dual light tooth cup 48 comprises a base, a left arm 51, and a right arm 52. Dual light tooth cup 48 is a rigid, semi-rigid, flexible, elastic, or resilient structural member that houses or retains the U-member 42, left tine section 43, and right tine section 44 of electrical ribbon or wiring assembly 36. Dual light tooth cup 48 has a distal end, a proximal end, a camera side 49, a tooth side 50, a left side, and a right side. Distal end is the end of dual light tooth cup 48 that is furthest from the operator during operation of two-piece bilateral illumination attachment for dental camera 5. Proximal end is the end of dual light tooth cup 48 that is closest to the operator during operation of two-piece bilateral illumination attachment for dental camera 5. Camera side 49 faces or is adjacent to dental camera 100 when two-piece bilateral illumination attachment for dental camera 5 is attached to dental camera 100. Tooth side 50 faces or is adjacent to the patient's tooth during use of the two-piece bilateral illumination attachment for dental camera 5. Left side is located on the operator's left side when facing the camera side 49 of dual light tooth cup 48. Right side is located on the operator's right side when facing the camera side 49 of dual light tooth cup 48. Base is a rigid, semi-rigid, flexible, elastic, or resilient essentially planar member. One side of base is the camera side 49 and the other side of base is the tooth side 50. Dual light tooth cup 48 may be made from steel, metal, composite, plastic, polymer, rubber, elastomer, carbon fiber, fiberglass, epoxy, or similar.

The camera side 49 of dual light tooth cup 48 has a U-member recess 55. U-member recess 55 is a recess or gully in the camera side 49 of dual light tooth cup 48. U-member recess 55 is the inverse shape of U-member 42 so that U-member 42 may be inserted therein. There is a left arm socket 53 on the U-member recess 55. Left arm socket 53 is an internal channel or cavity running from the camera side 49 of dual light tooth cup 48, through a left arm 51, to exit laterally from the tooth end of left arm 51. There is a right arm socket 54 on the right side of U-member recess 55. Right arm socket 54 is an internal channel or cavity running from the camera side 49 of dual light tooth cup 48, through a right arm 52, to exit laterally from the tooth end of right arm 52, to face the exit of left arm socket 53, as depicted.

The camera side 49 of dual light tooth cup 48 also has a camera port 56. Camera port 56 is an open space, void, or aperture through the base of dual light tooth cup 48 penetrating from the camera side 49 to the tooth side 50. Camera port 56 on dual light tooth cup 48 aligns with camera port 35 on tooth cup ledge 32 when dual light tooth cup 48 is properly installed or attached to tooth cup ledge 32. Camera port 56 functions to allow to allow the image sensor on the distal end of dental camera 100 to have an open path or clear field of view of the tooth during use of the two-piece bilateral illumination attachment for dental camera 5 for sub-enamel illumination or bilateral illumination of the tooth. An open path or clear field of view between the image sensor and the tooth is required to allow the image sensor on dental camera 100 to capture an image or take a picture of the tooth during sub-enamel illumination or bilateral illumination of the tooth.

The tooth side 50 of dual light tooth cup 48 has a left arm 51 protruding upwards or outwards therefrom. Left arm 51 is a rigid, semi-rigid, flexible, elastic, or resilient oblong structural member that houses or retains the left tine section 43 of electrical ribbon or wiring assembly 36. Left arm 51 is a rigid, semi-rigid, flexible, elastic, or resilient hollow oblong protrusion extending outwards from tooth side 50. Left arm 51 has a camera end that is located adjacent to dental camera 100 when two-piece bilateral illumination attachment for dental camera 5 is properly attached to dental camera 100. Left arm 51 has a tooth end that is located adjacent to patient's tooth when two-piece bilateral illumination attachment for dental camera 5 is in use. Left arm has four sides. Left arm 51 has a longitudinal axis that is perpendicular to the plane of tooth side 50 and the plane of the base of dual light tooth cup 48. The longitudinal axis of left arm 51 is concentric with left arm socket 53 on the camera side 49. The hollow interior of left arm 51 is left arm socket 53. Left arm socket 53 is a longitudinal cavity, void, or conduit running along the longitudinal axis or length of left arm 51. Left arm socket 53 has a camera end that is located adjacent to dental camera 100 when two-piece bilateral illumination attachment for dental camera 5 is properly attached to dental camera 100. Camera end of left arm socket 53 extends to the U-member recess 55 on the camera side 49. Left arm socket 53 has a tooth end that is located adjacent to patient's tooth when two-piece bilateral illumination attachment for dental camera 5 is in use. The tooth end of left arm socket 53 extends to a lateral exit on the tooth end of left arm 51. Left arm 51 houses or retains the left tine section 43 of electrical ribbon or wiring assembly 36. Left arm 51 may optionally have a left crown line 57 on one of its sides. Left crown line 57 is a visible line or marking on the left arm 51 that is used to align with the crown of the target tooth in order to properly position and locate left light source 45 onto the target tooth to properly effectuate sub-enamel illumination or bilateral illumination of the target tooth.

The tooth side 50 of dual light tooth cup 48 has a right arm 52 protruding upwards or outwards therefrom. Right arm 52 is a rigid, semi-rigid, flexible, elastic, or resilient oblong structural member that houses or retains the right tine section 44 of electrical ribbon or wiring assembly 36. Right arm 52 is a rigid, semi-rigid, flexible, elastic, or resilient hollow oblong protrusion extending outwards from tooth side 50. Right arm 52 has a camera end that is located adjacent to dental camera 100 when two-piece bilateral illumination attachment for dental camera 5 is properly attached to dental camera 100. Right arm 52 has a tooth end that is located adjacent to patient's tooth when two-piece bilateral illumination attachment for dental camera 5 is in use. Right arm 52 has four sides. Right arm 52 has a longitudinal axis that is perpendicular to the plane of tooth side 50 and the plane of the base of dual light tooth cup 48. The longitudinal axis of right arm 52 is concentric with right arm socket 54 on the camera side 49. The hollow interior of right arm 52 is right arm socket 54. Right arm socket 54 is a longitudinal cavity, void, or conduit running along the longitudinal axis or length of right arm 52. Right arm socket 54 has a camera end that is located adjacent to dental camera 100 when two-piece bilateral illumination attachment for dental camera 5 is properly attached to dental camera 100. Camera end of right arm socket 54 extends to the U-member recess 55 on the camera side 49. Right arm socket 54 has a tooth end that is located adjacent to patient's tooth when two-piece bilateral illumination attachment for dental camera 5 is in use. The tooth end of right arm socket 54 extends to a lateral exit on the tooth end of right arm 52. Right arm 52 houses or retains the right tine section 44 of electrical ribbon or wiring assembly 36. Right arm 52 may optionally have a right crown line 58 on one of its sides. Right crown line 58 is a visible line or marking on the right arm 52 that is used to align with the crown of the target tooth in order to properly position and locate right light source 46 onto the target tooth to properly effectuate sub-enamel illumination or bilateral illumination of the target tooth.

The distal section 10 of two-piece bilateral illumination attachment for dental camera 5 is assembled as follows. First, the left and right tine sections 43,44 of electrical ribbon or wiring assembly 36 must each be tucked or threaded into the left and right arm sockets 53,54 of dual light tooth cup 48 respectively. The left tine section 43 must be carefully threaded into left arm socket 53 so that the left light source 45 is properly positioned over the lateral exit of left arm socket 53 on the tooth end of left arm 51. Left light source 45 must shine out of the lateral exit of left arm socket 53. The right tine section 44 must be carefully threaded into right arm socket 54 so that the right source 46 is properly positioned over the lateral exit of right arm socket 54 on the tooth end of right arm 52. Right light source 46 must shine out of the lateral exit of right arm socket 54. Next, the dual light tooth cup 48 and electrical ribbon or wiring assembly 36 is inserted into the clamshell structure of the distal section 10. The dual light tooth cup 48 and electrical ribbon or wiring assembly 36 is inserted into the locking key protrusion 20, elongated neck 30, end cap 31, and tooth cup ledge 32 being careful to position first and second electrical contacts 37,38 properly into locking key protrusion 20 and then rigidly attaching the clamshell halves together. Rigid attachment may be accomplished by any known means such as glue, adhesive, epoxy, welding, sonic welding, soldering, press-fit, or similar.

Proximal section 60 may be made from any known material that is rigid. Proximal section 60 is a rigid oblong structural member with a distal end 61, a proximal end 62, a left side 63, a right side 64, a concave side 65, a convex side 66, and a longitudinal axis. Distal end 61 is the end of proximal section 60 that is farthest from the operator during operation of two-piece bilateral illumination attachment for dental camera 5. Proximal end 62 is the end of proximal section 60 that is closest to the operator during operation of two-piece bilateral illumination attachment for dental camera 5. Concave side 65 has a general concave shape and a concave surface. Concave side 65 is the side of proximal section 60 that is faces or is adjacent to dental camera 100 when two-piece bilateral illumination attachment for dental camera 5 is properly attached to dental camera 100. Convex side 66 has a general convex shape and a convex surface. Convex side 66 is the side of proximal section 60 that is opposite of dental camera 100 when two-piece bilateral illumination attachment for dental camera 5 is properly attached to dental camera 100. Left side 63 is located on the operator's left side during operation of two-piece bilateral illumination attachment for dental camera 5. Right side 64 is located on the operator's right side during operation of two-piece bilateral illumination attachment for dental camera 5. Distal end 61 is specially sized and shaped to reversibly attach to distal section 10. This special shape includes locking key recess 70. Distal end 61 of proximal section 60 is reversibly attachable to the proximal end 12 of distal section 10 and vice versa. Concave side 65 is specially sized and shaped to make a slip-fit, press-fit, or snap-fit onto the larger diameter end 101 of dental camera 100. This special shape includes a half socket 90.

Proximal section 60 comprises an electronics compartment. Electronics compartment is a hollow compartment or void area underneath the convex surface of convex side 66 directly beneath on off switch 84. Electronics compartment functions to house a circuit board 80 and a battery 86. Proximal section 60 further comprises: a circuit board 80 and a battery 86. Circuit board 80 is a circuit board. Circuit board 80 comprises: a plurality of electrical circuits, a plurality of electrical contacts, first contact 81, second contact 82, and an on off switch 84. Electrical circuits include an integrated circuit or chip with read only memory and random access memory. Structurally, circuit board 80 is a rigid planar member with an upper surface and a lower surface. The upper surface faces convex side 66 and the lower surface faces concave side 65. First and second contacts 81,82 are each attached to or soldered to the upper surface of circuit boards 80. First and second contacts 81,82 are connected to and have electrical continuity with first and second electrical contacts 37,38 respectively when distal section is properly attached to proximal section 60. Proximal section 60 further comprises an on off switch 84. On off switch 84 is attached to or soldered to the upper surface of circuit board 80 and thus has electrical continuity therewith. A portion of on off switch 84 protrudes through convex side 66 in order to provide operator access thereto. Proximal section 60 may further comprise a battery tray 88 and a battery lid 89. Battery tray 88 is slidably attachable or reversibly attachable to circuit board 80. Battery tray 88 is a tray that holds battery 86. Battery 86 is placed within battery tray 88, which is attached to circuit board 80. Battery lid 89 is a lid or cap to electronics compartment. Battery 86 is installed and replaced in the typical way that batteries are installed and replaced. Battery 86 may be any known type of battery. In best mode, battery 86 is a button-type battery.

Concave side 65 is specially sized and shaped to make a slip-fit, press-fit, or snap-fit onto the exterior surface of a dental camera 100. A portion of this special shape is half socket 90. Proximal section 60 may further comprises a half socket 90. Half socket 90 is located on the proximal end 62 of proximal section 60. Half socket 90 creates part of the general concave shape of concave side 65. Half socket 90 makes a snap-fit over the larger diameter end 101 of dental camera 100. Half socket 90 is a rigid hollow partial cylindrical member that is a "half-pipe" shape. Half socket 90 is a half pipe. Half socket 90 has an inner diameter, an outer diameter, a distal end, a proximal end, and a longitudinal axis. The inner diameter of half socket 90 is sized to make a snap-fit over the outer diameter of the larger diameter end 101 of dental camera 100. Rigid hollow partial cylindrical member is partial because a portion of the side of the hollow cylindrical member is void or removed to yield an open space. A portion of the side of the hollow cylindrical member is void or open. Both ends of rigid hollow partial cylindrical member are void or open. These voids allow for easier insertion, attachment, detachment, and removal of the two-piece bilateral illumination attachment for dental camera 5 onto the dental camera 100.

Half socket 90 comprises: a left wing 92, a right wing 94, a left wing tip 96, and a right wing tip 98. Left wing 92 and left wing tip 96 are located on the operator's left side when facing the convex side 66. Right wing 94 and right wing tip 98 are located on the operator's right side when facing the convex side 66. Left wing 92 and left wing tip 96 comprise the left half of the rigid hollow partial cylindrical member. Left wing 92 is rigid arced member or curved member with an inner diameter, outer diameter, a distal end, a proximal end, a first side, and a second side. The inside diameter of left wing 92 is sized to make a snap-fit over the larger diameter end 101 of dental camera 100. Left wing 92 is the wider portion or base portion of the rigid hollow partial cylindrical member on the left side. The first side of left wing 92 is contiguous with left side 63. The second side of left wing 92 is contiguous with left wing tip 96. Left wing tip 96 is the more narrow portion or tip portion of the rigid hollow partial cylindrical member on the left side. Left wing tip 96 is rigid arced member or curved member with an inner diameter, outer diameter, a distal end, a proximal end, a first side, and a second side. The inside diameter of left wing tip 96 is sized to make a snap-fit over the larger diameter end 101 of dental camera 100. The first side of left wing tip 96 is contiguous with the second side of left wing 92. The second side of left wing tip 96 is adjacent to the void section of the rigid hollow partial cylindrical member. The length of left wing tip 96 is about 25-75 percent of that of left wing 92. The width of left wing tip 96 is about 20-50 percent of that of left wing 92. Right wing 94 and right wing tip 98 comprise the right half of the rigid hollow partial cylindrical member. Right wing 94 is rigid arced member or curved member with an inner diameter, outer diameter, a distal end, a proximal end, a first side, and a second side. The inside diameter of right wing 94 is sized to make a snap-fit over the larger diameter end 101 of dental camera 100. Right wing 94 is the wider portion or base portion of the rigid hollow partial cylindrical member on the right side. The first side of right wing 94 is contiguous with right side 14. The second side of right wing 94 is contiguous with right wing tip 98. Right wing tip 98 is the more narrow portion or tip portion of the rigid hollow partial cylindrical member on the right side. Right wing tip 98 is rigid arced member or curved member with an inner diameter, outer diameter, a distal end, a proximal end, a first side, and a second side. The inside diameter of right wing tip 98 is sized to make a snap-fit over the larger diameter end 101 of dental camera 100. The first side of right wing tip 98 is contiguous with the second side of right wing 94. The second side of right wing tip 98 is adjacent to the void section of the rigid hollow partial cylindrical member. The length of right wing tip 98 is about 25-75 percent of that of right wing 94. The width of right wing tip 98 is about 20-50 percent of that of right wing 94. Wings 92,94 and wing tips 96,98 function to wrap-around the larger diameter end 101 of dental camera 100 and reversible attach thereto by press-fit or slip-fit. The void section between the second side of left wing tip 96 and the second side of right wing tip 98 functions to allow clearance space for the distal end or smaller diameter end 102 of dental cameral to be passed there through during attachment and detachment of two-piece bilateral illumination attachment for dental camera 5. This clearance space makes it much easier to attach and detach two-piece bilateral illumination attachment for dental camera 5 to dental camera 100. An alternate description of half socket 90 is that left wing 92, left wing tip 96, right wing 94, and right wing tip 98 collectively form a half pipe shape. The inner diameter of this half pipe is sized to make a snap-fit over the outer diameter of the larger diameter end 101 of dental camera 100. Left wing 92 forms left half of the wider base of the half pipe shape. Right wing 94 forms right half of the wider base of the half pipe shape. Left wing tip 96 forms the narrower tip or end of the half pipe shape on the left. Right wing tip 98 forms the narrower tip or end of the half pipe shape on the right. The half pipe shape spans about 190 to 330 degrees of a complete 360-degree circle or full pipe. Left wing 92 spans about 90 to 130 degrees of a complete circle. Left wing tip 96 spans about 5 to 30 degrees of a complete circle. Right wing 94 spans about 90 to 130 degrees of a complete circle. Right wing tip 98 spans about 5 to 30 degrees of a complete circle. The void section at the top of the half pipe functions to allow clearance space for the distal end or smaller diameter end 102 of dental cameral to be passed there through during attachment and detachment of two-piece bilateral illumination attachment for dental camera 5. This clearance space makes it much easier to attach and detach two-piece bilateral illumination attachment for dental camera 5 to dental camera 100.

Proximal section 60 further comprises a locking key recess 70. Locking key recess 70 is a rigid rectangular cuboid-shaped, cube-shaped protrusion, or key-shaped recess on the concave side 65 of proximal section 60 at the distal end 61 of proximal section 60 as depicted. Locking key recess 70 mates with a locking key protrusion 20 on distal section 10 when distal section 10 is properly attached to proximal section 60. Locking key recess 70 has a left surface 71, a right surface 72, a crown surface 73, and a proximal surface 74. Left surface 71 is located on the operator's left side during operation of two-piece bilateral illumination attachment for dental camera 5. Right surface 72 is located on the operator's right side during operation of two-piece bilateral illumination attachment for dental camera 5. Crown surface 73 is located on the concave side 65 of proximal section 60. Proximal surface 24 is located on the proximal end 62 of proximal section 60. Left surface 71, right surface 72, crown surface 73, and proximal surface 74 are each essentially planer members. Left surface 71, right surface 72, crown surface 73, and proximal surface 74 make up four sides of the rectangular cuboid-shaped or cube-shaped recess that is locking key recess 70. The other two sides of the rectangular cuboid-shaped or cube-shaped recess are open or void to allow clearance for insertion of the locking key protrusion 20.

Locking key recess 70 may further comprise: a left groove 77 and a right groove 76. Left groove 77 is a groove or linear depression on the left surface 71 of locking key recess 70.

Left groove 77 has a length, a width, a height, and a longitudinal axis. The longitudinal axis of left groove 77 may run parallel or perpendicular to that of proximal section 60. Left groove 77 is sized to make a slip-fit with a left rail 25 on locking key protrusion 20. Left rail 25 slides within left groove 77, along the longitudinal axis of left rail 25, when the distal section 10 is being attached to and/or detached from proximal section 60. Right groove 76 is a rail or linear protrusion on the right surface 72 of locking key recess 70. Right groove 76 has a length, a width, a height, and a longitudinal axis. The longitudinal axis of left groove 77 is parallel with that of right groove 76. Right groove 76 is sized to make a slip-fit with a right rail 26 on locking key protrusion 20. Right rail 26 slides within right groove 76, along the longitudinal axis of right rail 26, when the distal section 10 is being attached to and/or detached from proximal section 60.

Left and right rails 25,26 along with left and right grooves 77,76 function to guide and align locking key protrusion 20 properly within locking key recess 70 during attachment and/or detachment of distal section 10 and proximal section 60. Right and left rails 25,26 along with left and right grooves 77,76 also function to guide and align first, second, and third electrical contacts 37,38,39 properly to contact first, second, and third contacts 81,82,83 during attachment and/or detachment of distal section 10 and proximal section 60. When distal section 10 is properly attached to proximal section 60, there is electrical continuity between first electrical contact 37 and first contact 81. When distal section 10 is properly attached to proximal section 60, there is electrical continuity between second electrical contact 38 and second contact 82. When distal section 10 is properly attached to proximal section 60, there is electrical continuity between third electrical contact 41 and third contact 83.

Locking key recess 70 may further comprise: a left divot 79 and a right divot 78. Left divot 79 and right divot 78 are each a divot, indentation, or recess. Right divot 78 is on the right surface 72 of locking key recess 70. Right detent 28 nests within or catches within a right divot 78 on locking key recess 70 when distal section 10 is properly attached to proximal section 60. Left divot 79 is on the left surface 71 of locking key recess 70. Left detent 27 nests within or catches within a left divot 79 on locking key recess 70 when distal section 10 is properly attached to proximal section 60. Left and right detents 27,28 function with left and right divots 79,78 to rigidly lock and hold the distal section 10 onto the proximal section 60 when the two sections are properly attached or snapped together.

Dual light tooth cup 48 and other portions of distal section 60 touch or make contact with the inside of a patient's mouth during use of the two-piece bilateral illumination attachment for dental camera 5. Therefore these portions must be sterilized or discarded after use with a particular patient. Since the dual light tooth cup 48 contains expensive electronics and light sources, it is desirable to re-use the dual light tooth cups 48. This design allows for sterilization and re-use of the entire distal section 10 along with the dual light tooth cup 48.

In order to attach distal section 10 to proximal section 60, the locking key protrusion 20 on distal section 10 is aligned with and placed within the locking key recess 70 on proximal section 60 and pressed together until the left and right detents 27,28 on distal section 10 fall into or snap into the right and left divots 78,79 on proximal section 60 respectively. In order to detach distal section 10 to proximal section 60, the locking key protrusion 20 on distal section 10 is pushed out of or slid out of the locking key recess 70 on proximal section 60 until the left and right detents 27,28 on distal section 10 fall out of or snap out of the right and left divots 78,79 on proximal section 60 respectively.

In order to attach two-piece bilateral illumination attachment for dental camera 5 to a dental camera 100, the smaller diameter end 102 and the distal tip of dental camera 100 are inserted through the void section between left and right wing tips 96,98 and pushed towards the distal end 11 of distal section 10. Then, the smaller diameter end 102 and the distal tip of dental camera 100 are inserted through the locating collar 18 from its proximal end. Then, the smaller diameter end 102 and the distal tip of dental camera 100 are inserted into cup or socket shape of end cap 31 in order to snap into place. The snap signals a proper press-fit or slip-fit of two-piece bilateral illumination attachment for dental camera 5 to dental camera 100. The press-fit or slip-fit is reversible.

What is claimed is:

1. A two-piece bilateral illumination attachment for dental camera comprising: a distal section, a proximal section, and a means to reversibly attach said distal section to said proximal section, wherein, said distal section comprises: a locating collar, an elongated neck, an end cap, a tooth cup ledge, a dual light tooth cup, an electrical ribbon or wiring assembly, a distal end, and a proximal end, said locating collar is a rigid tapered cylindrical member, said elongated neck is an elongated rigid structural member with a distal end and a proximal end, said end cap is a rigid cup-shaped, socket-shaped, or U-shaped member, said tooth cup ledge is a rigid planar member, said dual light tooth cup is a rigid member with a base, a left arm, and a right arm, wherein, said left arm protrudes upwards or outwards from said base and said right arm protrudes upwards or outwards from said base, said electrical ribbon or wiring assembly is an assembly of two or more electrically conductive members with a first light source and a second light source connected thereto, said proximal end of said elongated neck is connected to said locating collar, said distal end of said elongated neck is connected said end cap, said tooth cup ledge is connected to said end cap, said dual light tooth cup is connected to said tooth cup ledge, said electrical ribbon or wiring assembly is installed within said elongated neck, said end cap, and said dual light tooth cup, said proximal section comprises: a circuit board, and a battery, said circuit board is a circuit board with a plurality of electrical circuits and a plurality of electrical contacts, said battery is a battery, said circuit board and said battery are installed within said proximal section, and said means to reversibly attach said distal section to said proximal section is a means to reversibly rigidly attach said distal end of said proximal section to said proximal end of said distal section.

2. A two-piece bilateral illumination attachment for dental camera comprising: a distal section, a proximal section, and a means to reversibly attach said distal section to said proximal section, wherein, said distal section comprises: a locating collar, an elongated neck, an end cap, a tooth cup ledge, a dual light tooth cup, an electrical ribbon or wiring assembly, a distal end, and a proximal end, said locating collar is a rigid tapered cylindrical member, said elongated neck is an elongated rigid structural member with a distal end and a proximal end, said end cap is a rigid cup-shaped, socket-shaped, or U-shaped member, said tooth cup ledge is a rigid planar member, said dual light tooth cup is a semi-ridged member with a base, a left arm, and a right arm, wherein, said left arm protrudes upwards or outwards from said base and said right arm protrudes upwards or outwards from said base, said electrical ribbon or wiring assembly is an assembly of two or more electrically conductive members with a first light source and a second light source connected thereto, said proximal end of said elongated neck is connected to said locating collar, said distal end of said elongated neck is connected said end cap, said tooth cup ledge is connected to said end cap, said dual light tooth cup is connected to said tooth cup ledge, said electrical ribbon or wiring assembly is installed within said elongated neck, said end cap, and said dual light tooth cup, said proximal section comprises: a circuit board, and a battery, said circuit board is a circuit board with a plurality of electrical circuits and a plurality of electrical contacts, said battery is a battery, said circuit board and said battery are installed within said proximal section, and said means to reversibly attach said distal section to said proximal section is a means to reversibly rigidly attach said distal end of said proximal section to said proximal end of said distal section.

3. A two-piece bilateral illumination attachment for dental camera comprising: a distal section and a proximal section, wherein, said distal section comprises: a locating collar, a locking key protrusion, an elongated neck, an end cap, a tooth cup ledge, a dual light tooth cup, and an electrical ribbon or wiring assembly, said locating collar is a rigid tapered cylindrical member with a distal end and a proximal end, said locking key protrusion is a rigid rectangular cuboid-shaped, cube-shaped protrusion, or key-shaped protrusion, said elongated neck is an elongated rigid structural member with a distal end and a proximal end, said end cap is a rigid cup-shaped, socket-shaped, or U-shaped member, said tooth cup ledge is a rigid planar member, said dual light tooth cup is a rigid member with a base, a left arm, and a right arm, wherein, said left arm protrudes upwards or outwards from said base and said right arm protrudes upwards or outwards from said base, said electrical ribbon or wiring assembly is an assembly of two or more electrically conductive members with a first light source and a second light source connected thereto, said locating collar is adjacent to or connected to said locking key protrusion, said proximal end of said elongated neck is connected to said locating collar and to said locking key protrusion, said distal end of said elongated neck is connected said end cap, said tooth cup ledge is connected to said end cap, said dual light tooth cup is connected to said tooth cup ledge, said electrical ribbon or wiring assembly is installed within said locking key protrusion, said elongated neck, said end cap, and said dual light tooth cup, said proximal section comprises: a locking key recess, a circuit board, and a battery, said locking key recess is a rigid rectangular cuboid-shaped, cube-shaped protrusion, or key-shaped recess, said circuit board is a circuit board with a plurality of electrical circuits and a plurality of electrical contacts, said battery is a battery, and said circuit board and said battery are installed within said proximal section.

4. A two-piece bilateral illumination attachment for dental camera comprising: a distal section and a proximal section, wherein, said distal section comprises: a locating collar, a locking key protrusion, an elongated neck, an end cap, a tooth cup ledge, a dual light tooth cup, and an electrical ribbon or wiring assembly, said locating collar is a rigid tapered cylindrical member with a distal end and a proximal end, said locking key protrusion is a rigid rectangular cuboid-shaped, cube-shaped protrusion, or key-shaped protrusion, said elongated neck is an elongated rigid structural member with a distal end and a proximal end, said end cap is a rigid cup-shaped, socket-shaped, or U-shaped member, said tooth cup ledge is a rigid planar member, said dual light tooth cup is a semi-rigid member with a base, a left arm, and a right arm, wherein, said left arm protrudes upwards or outwards from said base and said right arm protrudes upwards or outwards from said base, said electrical ribbon or wiring assembly is an assembly of two or more electrically conductive members with a first light source and a second light source connected thereto, said locating collar is adjacent to or connected to said locking key protrusion, said proximal end of said elongated neck is connected to said locating collar and to said locking key protrusion, said distal end of said elongated neck is connected said end cap, said tooth cup ledge is connected to said end cap, said dual light tooth cup is connected to said tooth cup ledge, said electrical ribbon or wiring assembly is installed within said locking key protrusion, said elongated neck, said end cap, and said dual light tooth cup, said proximal section comprises: a locking key recess, a circuit board, and a battery, said locking key recess is a rigid rectangular cuboid-shaped, cube-shaped protrusion, or key-shaped recess, said circuit board is a circuit board with a plurality of electrical circuits and a plurality of electrical contacts, said battery is a battery, and said circuit board and said battery are installed within said proximal section.

* * * * *